(12) United States Patent
Kevil et al.

(10) Patent No.: US 10,307,441 B2
(45) Date of Patent: *Jun. 4, 2019

(54) PHARMACEUTICAL FORMULATIONS OF NITRITE AND USES THEREOF

(71) Applicant: Board of Supervisors of Louisiana State University and Agricultural and Mechanical College, Baton Rouge, LA (US)

(72) Inventors: Christopher Kevil, Shreveport, LA (US); Anthony Giordano, Shreveport, LA (US); Douglas R Flanagan, Iowa City, IA (US); Panayiotis P Constantinides, Gurnee, IL (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/847,966

(22) Filed: Sep. 8, 2015

(65) Prior Publication Data

US 2016/0067279 A1 Mar. 10, 2016

Related U.S. Application Data

(62) Division of application No. 12/904,791, filed on Oct. 14, 2010.

(Continued)

(51) Int. Cl.
*A61K 33/00* (2006.01)
*A61K 9/20* (2006.01)

(Continued)

(52) U.S. Cl.
CPC ............ *A61K 33/00* (2013.01); *A61K 9/0053* (2013.01); *A61K 9/2068* (2013.01); *A61K 9/2866* (2013.01); *A61K 9/5042* (2013.01)

(58) Field of Classification Search
CPC . A61K 33/00; A61K 9/20; A61K 9/48; A61K 9/28; A61K 9/50
See application file for complete search history.

(56) References Cited

U.S. PATENT DOCUMENTS 2,914,446 A 11/1959 MacDonald et al.
4,650,484 A 3/1987 Shaw et al.
(Continued)

FOREIGN PATENT DOCUMENTS

EP 1 336 602 A1 8/2003
EP 2488035 A1 8/2012
(Continued)

OTHER PUBLICATIONS

Bondonno et al., Nutrients, 7: 1906-1915 (2015).*
(Continued)

*Primary Examiner* — Lakshmi S Channavajjala
(74) *Attorney, Agent, or Firm* — Charles G. Holoubek; Davis & Bujold, PLLC

(57) ABSTRACT

The present invention relates to pharmaceutical compositions of nitrites such as inorganic nitrites, or any pharmaceutically acceptable salts, solvates, or prodrugs thereof, and the medical use of these compositions. The pharmaceutical compositions, which can be formulated for oral administration, can provide immediate release or extended release of the nitrite ion ($NO_2^-$). The pharmaceutical compositions of the invention are useful, for example, for the treatment of chronic tissue ischemia.

7 Claims, 13 Drawing Sheets

Related U.S. Application Data

(60) Provisional application No. 61/251,483, filed on Oct. 14, 2009.

(51) Int. Cl.
*A61K 9/28* (2006.01)
*A61K 9/50* (2006.01)
*A61K 9/00* (2006.01)

(56) References Cited

U.S. PATENT DOCUMENTS

| | | | |
|---|---|---|---|
| 5,122,384 | A | 6/1992 | Paradissis et al. |
| 5,489,610 | A | 2/1996 | Fung et al. |
| 5,648,101 | A | 7/1997 | Tawashi |
| 5,770,645 | A | 6/1998 | Stamler et al. |
| 5,994,444 | A | 11/1999 | Trescony et al. |
| 6,641,839 | B1 | 11/2003 | Geoghegan et al. |
| 6,709,681 | B2 | 3/2004 | Benjamin et al. |
| 6,962,717 | B1 | 11/2005 | Huber et al. |
| 7,371,415 | B1 | 5/2008 | Wuh et al. |
| 8,568,793 | B2 | 10/2013 | Sherman et al. |
| 2003/0125714 | A1 | 7/2003 | Edgren et al. |
| 2003/0219494 | A1* | 11/2003 | Smith ............... A61K 31/00 424/608 |
| 2003/0219495 | A1 | 11/2003 | Juneau et al. |
| 2004/0006140 | A1 | 1/2004 | Kaesemeyer |
| 2005/0113409 | A1 | 5/2005 | Connor et al. |
| 2006/0083824 | A1 | 4/2006 | Manning et al. |
| 2006/0125714 | A1 | 6/2006 | Miller |
| 2006/0182815 | A1 | 8/2006 | Gladwin et al. |
| 2007/0010571 | A1 | 1/2007 | Garvey et al. |
| 2007/0154569 | A1 | 7/2007 | Gladwin et al. |
| 2007/0190209 | A1 | 8/2007 | Sinnott |
| 2009/0196930 | A1 | 8/2009 | Surber et al. |
| 2009/0297634 | A1 | 12/2009 | Friedman et al. |
| 2010/0092441 | A1 | 4/2010 | Lundberg et al. |
| 2010/0247682 | A1 | 9/2010 | Gladwin et al. |
| 2011/0039875 | A1* | 2/2011 | Singh ............... A61K 31/137 514/289 |
| 2011/0311653 | A1 | 12/2011 | Kevil et al. |
| 2012/0237617 | A1 | 9/2012 | Kevil |
| 2013/0170357 | A1 | 7/2013 | Anchan et al. |
| 2013/0209584 | A1 | 8/2013 | Kevil et al. |
| 2015/0110899 | A1 | 4/2015 | Kevil et al. |

FOREIGN PATENT DOCUMENTS

| | | |
|---|---|---|
| JP | 2005501069 A | 1/2005 |
| WO | WO-1994/01103 A1 | 1/1994 |
| WO | WO-00-003725 A1 | 1/2000 |
| WO | WO-00-053193 A1 | 9/2000 |
| WO | WO-01-17596 A1 | 3/2001 |
| WO | WO-03-013489 A1 | 2/2003 |
| WO | WO-2005-004884 A3 | 1/2005 |
| WO | WO-2005/007173 A1 | 1/2005 |
| WO | WO-2006/084912 A1 | 8/2006 |
| WO | WO-2006-128032 A3 | 11/2006 |
| WO | WO-2007/116102 A2 | 10/2007 |
| WO | WO-2008/105730 A1 | 9/2008 |
| WO | WO-2008/105731 A1 | 9/2008 |
| WO | WO-2008/153762 A2 | 12/2008 |
| WO | WO-2009-065142 A2 | 5/2009 |
| WO | WO-2010-036236 A1 | 4/2010 |
| WO | WO-2010-147742 A9 | 12/2010 |
| WO | WO-2011-047161 A1 | 4/2011 |
| WO | WO-2012-135623 A1 | 10/2012 |
| WO | WO-2012-142413 A2 | 10/2012 |

OTHER PUBLICATIONS

Colorcon, Opadry Enteric Application Data, accessed at https://www.colorcon.com Nov. 3, 2016 (Jan. 2009).*

"In High Blood Pressure," The Canadian Medical Association Journal p. xliii, 1928.

"Peripheral arterial disease in people with diabetes," Diabetes Care 23(12):3333-3341 (2003).

Blood et al., "In Vitro and in vivo kinetic handling of nitrite in blood: Effects of varying hemoglobin exygen saturation," Am J Physiol Heart Circ Physiol. 293:H1508-H1517 (2007).

Bryan et al., "Dietary nitrite supplementation protects against myocardial ischemia-repurfusion injury," Proc Natl Acad Sci USA 104(48):19144-19149 (2007).

Contreras, et al. "The role of nitric oxide in the post-ischemic revascularization process," Pharmacol Ther. 112(2):553-63 (2006).

Cooke et al., "Nitric Oxide and Angiogenesis," Circulation, 105:2133-2135 (2002).

Cosby et al., "Nitrite reduction to nitric oxide by deoxyhemoglobin vasodilates the human circulation," NatMed. 9(12): 1498-1505 (2003).

Croft et al., "Ultrastructural studies of wound healing in mouse skin," J Anat 106:63-77 (1970).

Duncan et al., "Chemical generation of nitric oxide in the mouth from the enterosalivary circulation of dietary nitrate," Nat. Med., 1:546-551 (1995).

Green et al., "Analysis of nitrate, nitritem and [15N]nitrate in biological fluids," Anal Biochem., 126:131-138 (1982).

Greenberg, et al., "Nitro containing L-arginine analogs interfere with assays for nitrate and nitrite," Life Sci. 57(21):1949-61 (1995).

Greenway et al., "single-dose pharmacokinetics of different oral sodium nitrite formulations in diabetes patients," Diabetes Technol Ther. 14(7):552-560 (2012).

Jacoby et al., "Acute myocardial infarction in the diabetic patient: Pathophysiology, clinical couse and prognosis," J Am Coll Cardiol 20(3):736-44 (1992).

Jadeski, "Nitric oxide synthase inhibition by N(G)-nitro-L-arginine methyl ester inhibits tumor induced angiogenesis in mammary tumors," Am J Pathol. 155(4):1381-90 (1999).

Jung et al., "Early Intravenous Infusion of Sodium Nitrite Protects Brain Against In Vivo lschemia-Reperfusion Injury," Stroke 37:2744-2750 (2006).

Kenjale et al., "Dietary nitrate supplementation enhances exercise performance in peripheral arterial disease," J Appl. Physiol. 110:1592-1591 (2011).

Kevil, et al. "Inorganic nitrite therapy: historical perspective and future directions," Free Radic Bioi Med. 51 (3):576-93 (2011).

Kumar et al., "Nitrite enhances ischemia-induced angiogenesis by Nitric Oxide dependent pathway," FASEB Journal, Apr. 2007, Meeting abstract.

Moshage et al., "Nitrite and nitrate determinations in plasma: a critical evaluation," Clin Chem. 41 (6): 892-896, 1995.

Notice of Judgment Case No. 4151. Adulteration and misbranding of Natrico tablets. *U.S.* v. *140 Bottles* p. 147 (1954), accessed at http://archive.nim.nih.gov/fdanj/handle/123456789/12581.

Notices of Judgment Case 2310, Adulteration and alleged misbranding of drug tablets. *U.S.* v. *Charles H. Dietz, Inc.* p. 47-48 (1949), accessed at http://archive.nim.nih.gov/fdanj/handle/123456789/11149.

Pluta et al., "Sodium Nitrite as a therapeutic agent for central nervous system diseases," Surgical Neurology, 66:5-10 (2006).

Presley et al., "Acute effect of a high nitrate diet on brain perfusion in older adults," Nitric Oxide 24(1): 34-42, 2011.

Rikitake, et al., "Involvement of endothelial nitric oxide in sphingosine-1-phosphate-induced angiogenesis," Arterioscler Thromb Vasc Biol. 22(1 ):1 08-14 (2002).

Sun et al., "Measurement of nitric oxide production in biological systems by using griess reaction assay," Sensors 3: 276-284, 2003.

Sun, "Induction of angiogenesis by heat shock protein 90 mediated by protein kinase Akt and endothelial nitric oxide synthase," Arterioscler Thromb Vasc Biol. 24(12):2238-44 (2004).

Tripathi et al., "Effect of superoxide dismutase and acified sodium nitrate on infarct size following ischemia and reperfusion in dogs," Indian J Physiol Pharmacol 41(3):248-56 (1997).

Tsuchiya et al., "Nitrite is an alternative source of NO in vivo," Am J Physiol Heart Circ Physiol 288:H2163-2170 (2005).

(56) References Cited

OTHER PUBLICATIONS

Verma, et al., "A self-fulfilling prophecy: C-reactive protein attenuates nitric oxide production and inhibits angiogenesis," Circulation. 106(8):913-9 (2002).
Vitecek, et al., "Arginine-based inhibitors of nitric oxide synthase: therapeutic potential and challenges" Mediators Inflamm. 2012(318087):1-22 (2012).
Wagner et al., "Metabolic Fate of an Oral Dose of 15N-labeled Nitrate in Humans: Effect of Diet Supplementation with Ascorbic Acid," Cancer Res. 43:1921-1925 (1983).
Weller et al., "The effects of topical treatment with acidified nitrite on wound healing in normal and diabetic mice," Nitric Oxide, 15(4):395-359 (2006).
Zhang et al., "Nitric Oxide Enhances Angiogenesis via Synthesis of Vascular Endothelial Growth Factor and cGMP After Stroke in the Rat," Circulation Research, 92:308-313 (2003).
Ziche et al., "Nitric Oxide Mediates Angiogenesis In Vivo and Endothelial Cell Growth and Migration In Vitro Promoted by Substance P," J. Clin. Invest., 94:2036-2044, (1994).
Allen et al., "Plasma Nitrite Response and Arterial Reactivity Differentiate Vascular Health and Performance," Nitric Oxide, 20:231-237 (2009).
Combet et al, "Diet, gastric nitrosation and stomach cancer," Comparative Biochemistry and Physiology, Part A 146:S61 (2007) (Abstract only).
Dejam et al., "Nitrite Infusion in Humans and Nonhuman Primates: Endocrine Effects, Pharmacokinetics, and Tolerance Formation," Circulation, 116:1821-1831 (2007).
Duranski et al., "Cytoprotective effects of nitrite during in vivo ischemia-reperfusion of the heart and liver," J Clin Invest. 115(5):1232-1240 (2005).
Grosse et al., "Carcinogenicity of nitrate, nitrite, and cyanobacterial peptide toxins," Lancet Oncology 7:628-629 (2006).
Hunault et al., "Bioavailability of Sodium Nitrite from an Aqueous Solution in Healthy Adults," Toxicology Letters, 190(1):48-53 (2009).
Kohn et al., "Pharmacokinetics of Sodium Nitrite-Induced Methemoglobinemia in the Rat," *Drug Metabolism and Disposition*, 30(6):676-683 (2002).
Kumar et al., "Chronic Sodium Nitrite Therapy Augments Ischemia-Induced Angiogenesis and Arteriogenesis," *PNAS*, 105(21):7540-7545 (2008).
Mazzone et al., "A Lifeline for Suffocating Tissues," Nature, 453:1194-1195 (2008).
Medin et al., "Nitrite-Derived Nitric Oxide: A Possible Mediator of 'Acidic-Metabolic' Vasodilation," Acta Physiol. Scand. 171:9-16 (2001).
Namba et al., "Angiogenesis Induced by Endothelial Nitric Oxide Synthase Gene Through Vascular Endothelial Growth Factor Expression in a Rat Hindlimb Ischemia Model," Circulation 108: 2250-2257, 2003.
van Velzen et al., "The Oral Bioavailability of Nitrate from Nitrate-Rich Vegetables in Humans," Toxicology Letters, 181:177-181 (2008).
American Diabetes Association (Diabetes Care, 2003, vol. 26, pp. 3333-3341).
Kleinbongard et al., Free Radical Biology & Medicine, 40: 295-302 (2006).

* cited by examiner

Formulation #1 ($y = -0.0093x^2 + 0.1761x + 0.2879$)

Formulation #2 ($y = -0.0132x^2 + 0.1789x + 0.4361$)

Formulation #5 ($y = -0.0147x^2 + 0.203x + 0.3674$)

Formulation #9 ($y = -0.0129x^2 + 0.2126x + 0.0921$)

Formulation 9C (y = 0.125x + 9E-16)

Formulation 10C ($y = -0.0286x^2 + 0.3653x + 0.0041$):

Formulation 12 (y = -0.0158x² + 0.2536x + 0.2111):

Formulation 12C (y = -0.0185x$^2$ + 0.2886x + 0.0615)

Formulation 13  (y = -0.0021 x2 + 0.0487 x + 0.01597)

Formulation control (80 mg immediate release; 100% release over 30 minutes)

PHARMACEUTICAL FORMULATIONS OF NITRITE AND USES THEREOF

CROSS-REFERENCE TO RELATED APPLICATIONS

This application is a divisional of U.S. Non-Provisional application Ser. No. 12/904,791, filed Oct. 14, 2010 which claims the benefit of U.S. Provisional Application No. 61/251,483, filed Oct. 14, 2009, which are hereby incorporated by reference.

BACKGROUND OF THE INVENTION

The present invention relates to pharmaceutical compositions of nitrites and the medical use of these compositions.

Chronic tissue ischemia, i.e., persistent restriction of blood supply to a tissue, can impair tissue function and result in tissue and organ damage, thus contributing significantly to human morbidity and mortality. The chronic tissue ischemia can stem from any of a wide range of medical conditions that result in the persistent or recurring restriction of blood supply to the tissue, e.g., disorders such as peripheral artery disease, type 1 or type 2 diabetes, atherosclerotic cardiovascular disease, intermittent claudication, critical limb ischemic disease, stroke, myocardial infarction, inflammatory bowel disease, and peripheral neuropathy; traumatic injuries such as wounds, burns, lacerations, contusions, bone fractures, infections, or surgical procedures; congenital malformations such as hernias, cardiac defects and gastrointestinal defects. Thus, chronic tissue ischemia can occur in a variety of tissue types including, for example, skeletal muscle, smooth muscle, cardiac muscle, neuronal tissue, skin, mesenchymal tissue, connective tissue, gastrointestinal tissue and bone. Accordingly, there is a continuing need for therapeutic strategies that restore blood supply to affected regions.

SUMMARY OF THE INVENTION

In general, in a first aspect, the invention features a pharmaceutical composition that includes an effective amount of inorganic nitrite, or a pharmaceutically acceptable salt, solvate, or prodrug thereof, and a pharmaceutically acceptable excipient. Desirably, administration of the pharmaceutical composition to a human results in a plasma concentration of nitrite ion that is maintained between 0.05 µM and 10 µM (e.g., between 0.1 µM and 10 µM, 0.5 µM and 5 µM, 0.1 µM and 3 µM, or 0.1 µM and 1 µM) for up to 14 hours.

In other embodiments, the inorganic nitrite is administered at a dose that is between 0.1 µg-10 mg/kg weight of the human (e.g., between 1 µg-5 mg/kg, 0.05-10 mg/kg, 0.1-5 mg/kg, 0.5-5 mg/kg, 0.5-3 mg/kg, 0.1-1.5 mg/kg, 0.1-0.35 mg/kg, 0.35-0.75 mg/kg, or 0.75-1 mg/kg). In still other embodiments, the dose is 0.25 mg/kg, 0.5 mg/kg, or 1 mg/kg.

In certain embodiments, the pharmaceutical composition includes 0.5-5.0 mmol (e.g., 1.0-4.0 mmol) of nitrite ion ($NO_2^-$).

In other embodiments, the nitrite ion is provided as $NaNO_2$, $KNO_2$, or arginine nitrite. In certain embodiments, the nitrite ion is provided as $NaNO_2$.

In still other embodiments, the pharmaceutical composition is formulated for oral administration. In further embodiments, pharmaceutical composition is a tablet or capsule.

In other embodiments, the pharmaceutical composition includes an excipient that is an alkanizing agent, a glidant, a lubricant, a bulking agent, a polymer that comprises cellulose, or polyethylene glycol, or any combination thereof. In still other embodiments, the pharmaceutical composition includes a pharmaceutically acceptable excipient (e.g., a pH sensitive polymer or a biodegradable polymer) for delayed release of the inorganic nitrite, such that, when orally administered to a human subject, the inorganic nitrite is not substantially released in the stomach of the subject. In further embodiments, an enteric coating includes the pharmaceutically acceptable excipient for delayed release of the inorganic nitrite. In certain embodiments, the pharmaceutically acceptable excipient is ethyl cellulose, cellulose acetate, cellulose acetate butyrate, cellulose triacetate, cellulose acetate phthalate (CAP), cellulose trimellitate, hydroxypropylmethylcellulose acetate succinate, or Eudragit® L or S. In further embodiments, the pharmaceutical composition further includes polyethylene glycol and/or a plasticizer.

In some embodiments, the pharmaceutical composition is a multiparticulate dosage form. In certain embodiments, the multiparticulate dosage form includes pellets or granules. In further embodiments, the pellets or granules are coated with a coating layer that includes a biodegradable polymer (e.g., a polysaccharide such as alginate, pectin, carrageenan, chitosan, dextran, shellac, or xanthan gum, or any mixture thereof).

In a second aspect, the invention relates to a pharmaceutical composition formulated for oral administration that includes an effective amount of inorganic nitrite, or a pharmaceutically acceptable salt, solvate, or prodrug thereof, and a pharmaceutically acceptable excipient for delayed release of the inorganic nitrite, such that, when orally administered to a human subject, the inorganic nitrite is not substantially released in the stomach of the subject. In certain embodiments, the pharmaceutical composition is a tablet or capsule.

In a third aspect, the invention features a pharmaceutical composition suitable for oral administration comprising: (a) an effective amount of inorganic nitrite, or a pharmaceutically acceptable salt, solvate, or prodrug thereof; and (b) an enteric coating layer. Desirably, the pharmaceutical composition is formulated such that, when administered to a human subject, the inorganic nitrite is not substantially released in the stomach of the subject.

In certain embodiments, administration of the pharmaceutical composition to a human results in a plasma concentration that is maintained between 0.05 µM and 10 µM (e.g., between 0.1 µM and 10 µM, 0.5 µM and 5 µM, 0.1 µM and 3 µM, or 0.1 µM and 1 µM).

In other embodiments, the inorganic nitrite is administered at a dose that is between 0.1 µg-10 mg/kg weight of the human (e.g., between 1 µg-5 mg/kg, 0.05-10 mg/kg, 0.1-5 mg/kg, 0.5-5 mg/kg, 0.5-3 mg/kg, 0.1-1.5 mg/kg, 0.1-0.35 mg/kg, 0.35-0.75 mg/kg, or 0.75-1 mg/kg). In further embodiments, the dose is 0.25 mg/kg, 0.5 mg/kg, or 1 mg/kg.

In still other embodiments, the pharmaceutical composition includes 0.5-5.0 mmol (e.g., 1.0-4.0 mmol) of nitrite ion ($NO_2^-$).

In certain embodiments, the nitrite ion is provided as $NaNO_2$, $KNO_2$, or arginine nitrite. In further embodiments, the nitrite ion is provided as $NaNO_2$.

In other embodiments, the enteric coating layer includes a pharmaceutically acceptable excipient is a pH sensitive polymer or a biodegradable polymer.

In still other embodiments, the pharmaceutical composition is a tablet or capsule.

In any of the foregoing aspects, the plasma concentration of nitrite ion is maintained for a period of up to 14 hours (e.g., 4-14 hours, 6-12 hours, or 6-10 hours). The periods of maintained plasma concentration can occur, e.g., during and/or after the time of peak plasma concentration. In some embodiments, 30-50% of the nitrite ion is released in the first hour and the remainder of the nitrate ion is released in the following 2-14 hours.

In another aspect, the invention features a method for treating or preventing chronic tissue ischemia in a human. Desirably, the method includes the administration of any of the pharmaceutical compositions described herein to a human. In certain embodiments, the administration is oral.

In still another aspect, the invention features a method of supplementing deficits in circulating nitrite found in a patient, wherein said method comprises the administration of any of the pharmaceutical compositions described herein to a human The present invention relates to pharmaceutical compositions of nitrite (e.g., inorganic nitrite) and use of these compositions for the treatment of chronic tissue ischemia, including chronic tissue ischemia associated with a disorder, trauma or a congenital defect.

As used herein, the term "delayed release" refers to a pharmaceutical preparation, e.g., an orally administered formulation, which passes through the stomach substantially intact and dissolves in the small and/or large intestine (e.g., the colon). In some embodiments, delayed release of the active agent (e.g., nitrite as described herein) results from the use of an enteric coating of an oral medication (e.g., an oral dosage form).

The term an "effective amount" of an agent, as used herein, is that amount sufficient to effect beneficial or desired results, such as clinical results, and, as such, an "effective amount" depends upon the context in which it is being applied.

The terms "extended release" or "sustained release" interchangeably refer to a drug formulation that provides for gradual release of a drug over an extended period of time, e.g., 6-12 hours or more, compared to an immediate release formulation of the same drug. Preferably, although not necessarily, results in substantially constant blood levels of a drug over an extended time period that are within therapeutic levels and fall within a peak plasma concentration range that is between, for example, 0.05-10 µM, 0.1-10 µM, 0.1-5.0 µM, or 0.1-1 µM.

As used herein, the terms "formulated for enteric release" and "enteric formulation" refer to pharmaceutical compositions, e.g., oral dosage forms, for oral administration able to provide protection from dissolution in the high acid (low pH) environment of the stomach. Enteric formulations can be obtained by, for example, incorporating into the pharmaceutical composition a polymer resistant to dissolution in gastric juices. In some embodiments, the polymers have an optimum pH for dissolution in the range of approx. 5.0 to 7.0 ("pH sensitive polymers"). Exemplary polymers include methacrylate acid copolymers that are known by the trade name Eudragit® (e.g., Eudragit® L100, Eudragit® S100, Eudragit® L-30D, Eudragit® FS 30D, and Eudragit® L100-55), cellulose acetate phthalate, cellulose acetate trimellitiate, polyvinyl acetate phthalate (e.g., Coateric®), hydroxyethylcellulose phthalate, hydroxypropyl methylcellulose phthalate, or shellac, or an aqueous dispersion thereof. Aqueous dispersions of these polymers include dispersions of cellulose acetate phthalate (Aquateric®) or shellac (e.g., MarCoat 125 and 125N). An enteric formulation reduces the percentage of the administered dose released into the stomach by at least 50%, 60%, 70%, 80%, 90%, 95%, or even 98% in comparison to an immediate release formulation. Where such a polymer coats a tablet or capsule, this coat is also referred to as an "enteric coating."

The term "pharmaceutical composition," as used herein, represents a composition containing a compound described herein (e.g., inorganic nitrite, or any pharmaceutically acceptable salt, solvate, or prodrug thereof), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic or inorganic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate" or "solvate," as used herein, means a compound of the invention wherein molecules of a suitable solvent are incorporated in the crystal lattice. A suitable solvent is physiologically tolerable at the administered dose. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, refers to prophylactic treatment or treatment that prevents one or more symptoms or conditions of a disease, disorder, or conditions described herein (e.g., chronic tissue ischemia). Treatment can be initiated, for example, prior to ("pre-exposure prophylaxis") or following ("post-exposure prophylaxis") an event that precedes the onset of the disease, disorder, or conditions. Treatment that includes administration of a compound of the invention, or a pharmaceutical composition thereof, can be acute, short-term, or chronic. The doses administered may be varied during the course of preventive treatment.

The term "prodrug," as used herein, represents compounds which are rapidly transformed in viveo to the parent compound of the above formula. Prodrugs also encompass bioequivalent compounds that, when administered to a human, lead to the in vivo formation of nitrite ion ($NO_2^-$) or nitrous oxide (NO). A thorough discussion is provided in T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, each of which is incorporated herein by reference. Preferably, prodrugs of the compounds of the present invention are pharmaceutically acceptable such as those described in EP 1336602A1, which is herein incorporated by reference.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. As used herein, the terms "treating" and "treatment" can also refer to delaying the onset of, retarding or reversing the progress of, or alleviating either the disease or condition to which the term applies, or one or more symptoms of such disease or condition.

The term "unit dosage forms" refers to physically discrete units suitable as unitary dosages for human subjects and other mammals, each unit containing a predetermined quantity of active material calculated to produce the desired therapeutic effect, in association with any suitable pharmaceutical excipient or excipients.

As used herein, the term "plasma concentration" refers to the amount of nitrite ion present in the plasma of a treated subject (e.g., as measured in a rabbit using an assay described below or in a human).

Other features and advantages of the invention will be apparent from the following Detailed Description, the drawings, and the claims.

DETAILED DESCRIPTION

Figure 1:
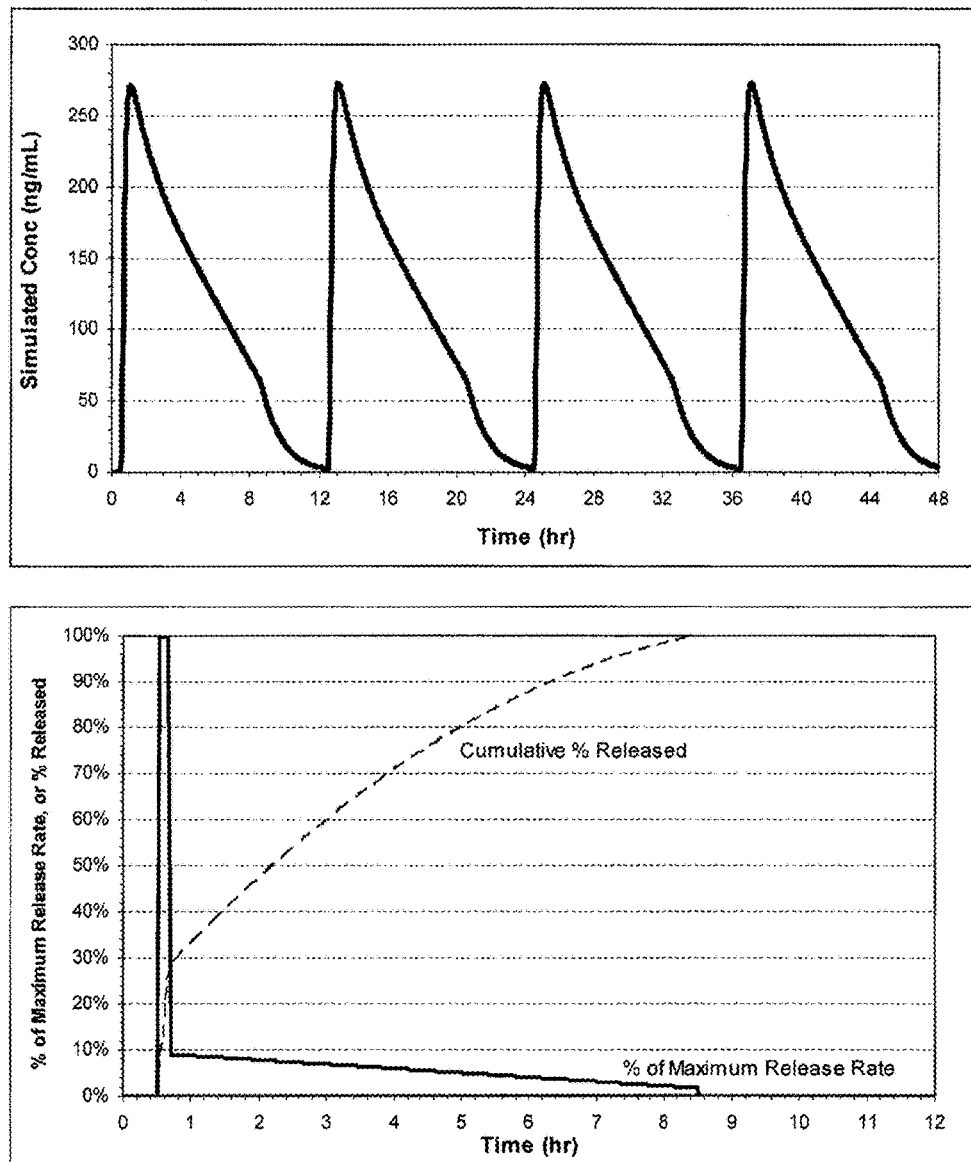
FIGS. 1-10 show the results from simulations of nitrite plasma levels from controlled release formulation 1 (FIG. 1), formulation 2 (FIG. 2), formulation 5 (FIG. 3), formulation 9 (FIG. 4), formulation 9C (FIG. 5), formulation 10C (FIG. 6), formulation 12 (FIG. 7), formulation 12C (FIG. 8), and formulation 13 (FIG. 9), as well as from a control immediate release formulation (FIG. 10). Note: The polynomial fit of FIG. 9 predicts only 27% of the 80 mg tablet contents is released over an 8 hour period (21.6 mg released). The simulation assumes that only 27% of the 80 mg dose is released within 8 hours, and then the tablet releases no more material. The maximum possible release predicted by this polynomial is approximately 29%, which requires approximately 11.5 hours.
Figure 2:
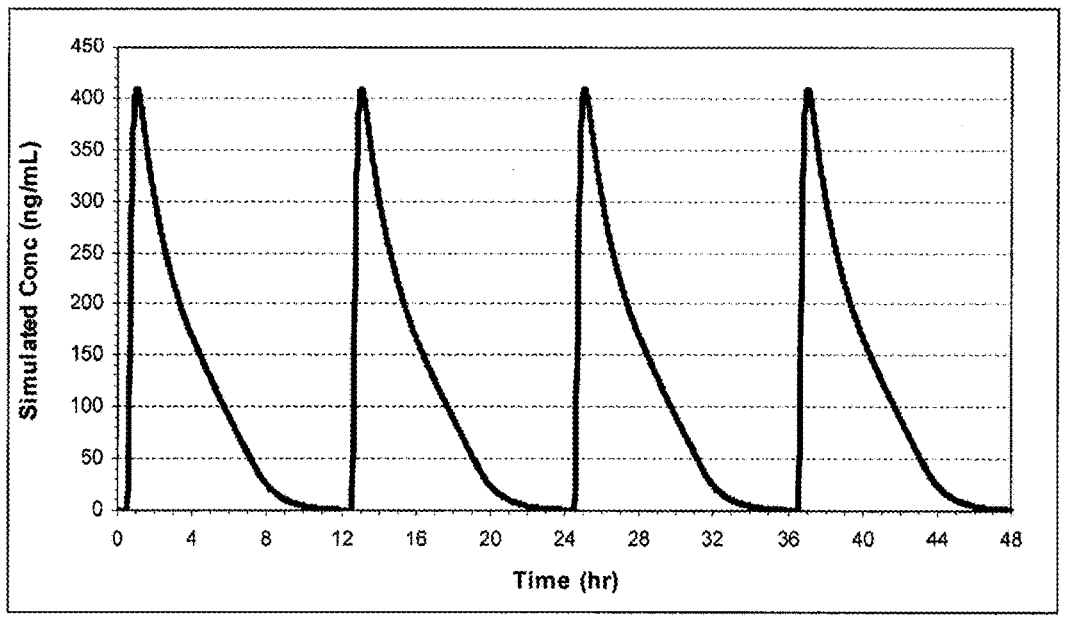
Figure 2:
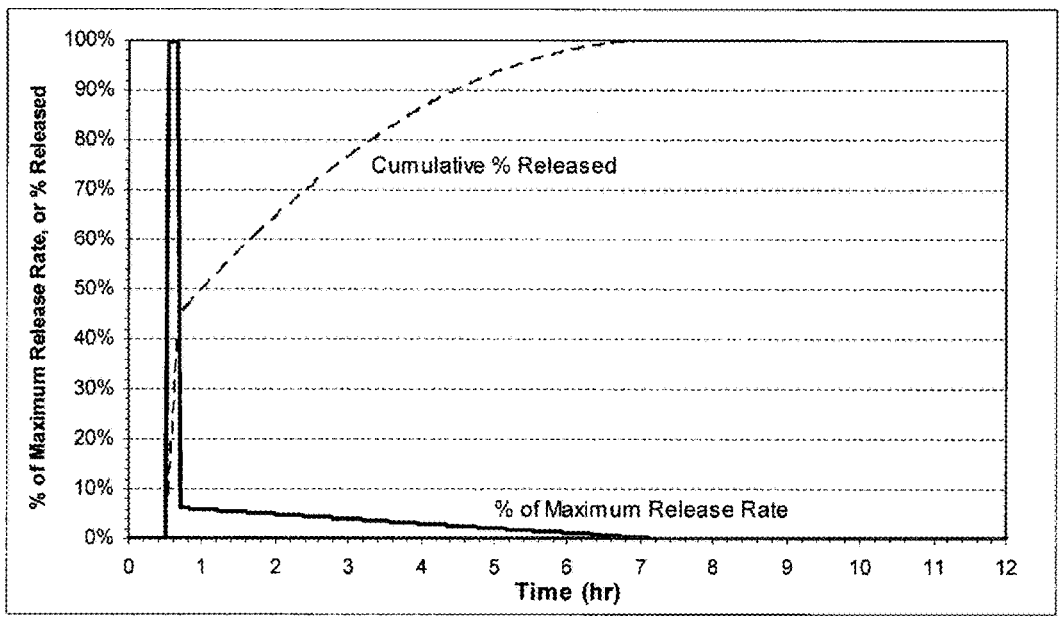
Figure 3:
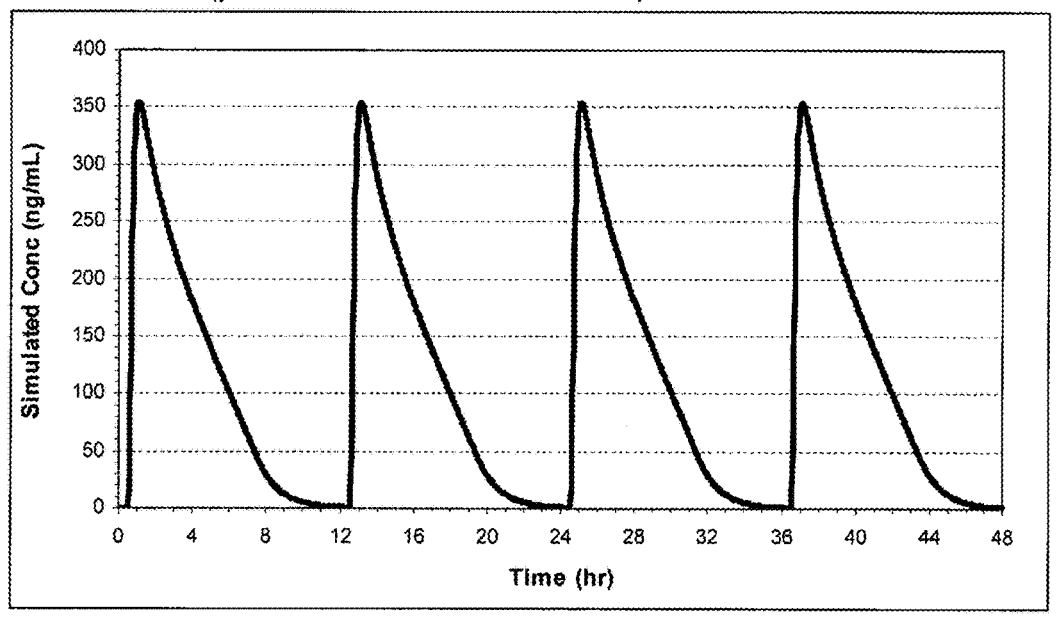
Figure 3:
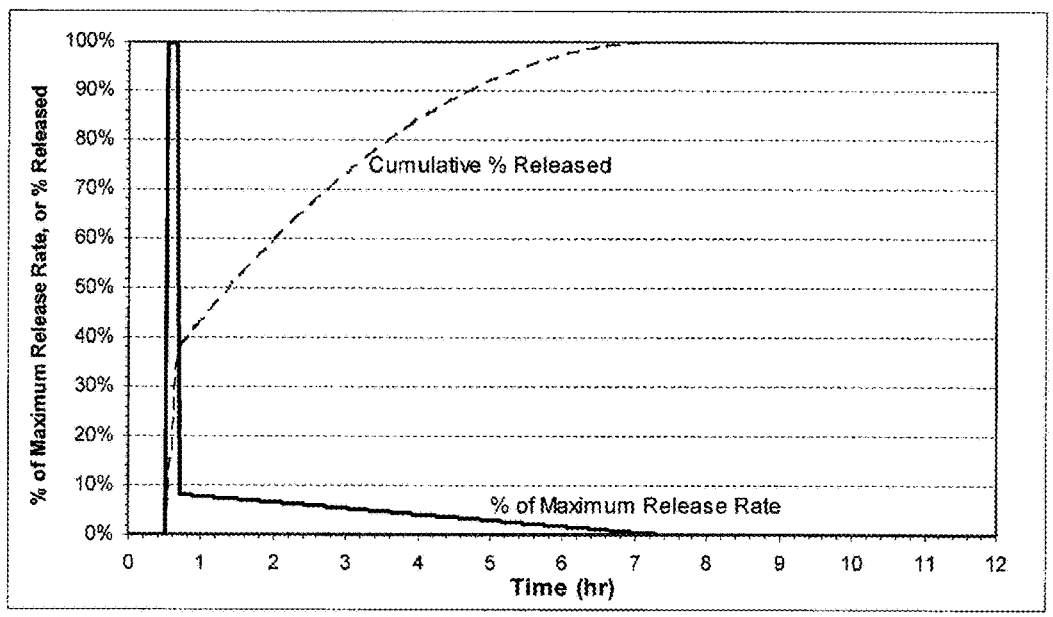
Figure 4:
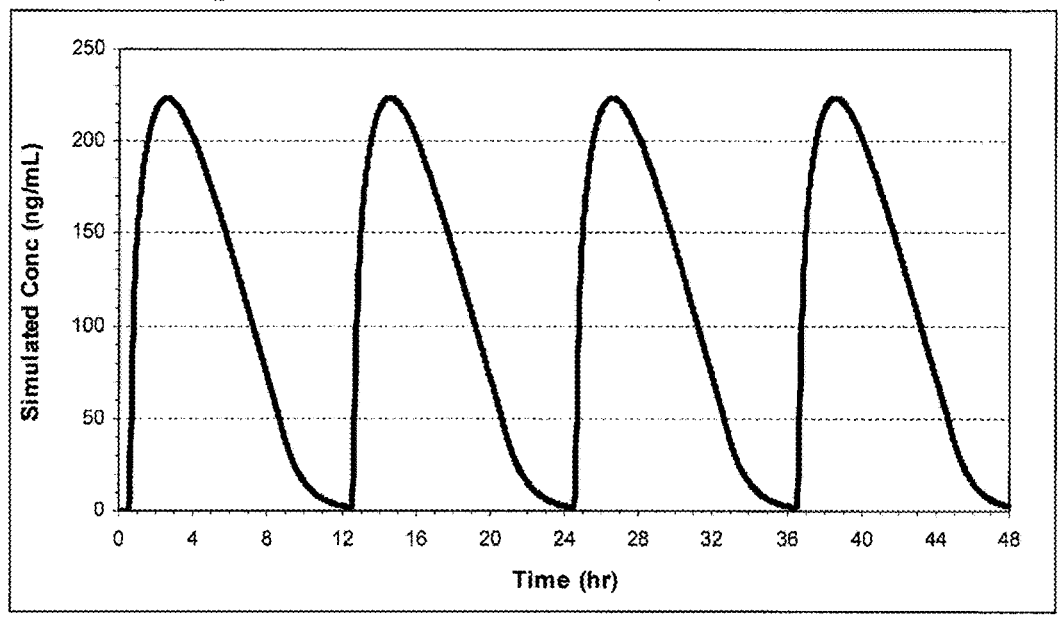
Figure 4:
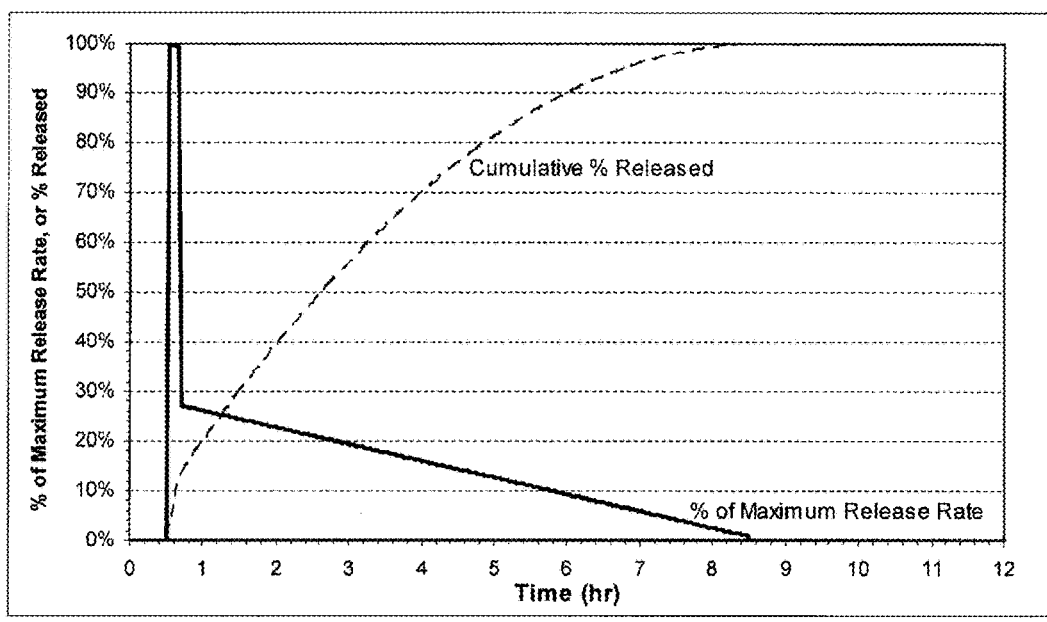
Figure 5:
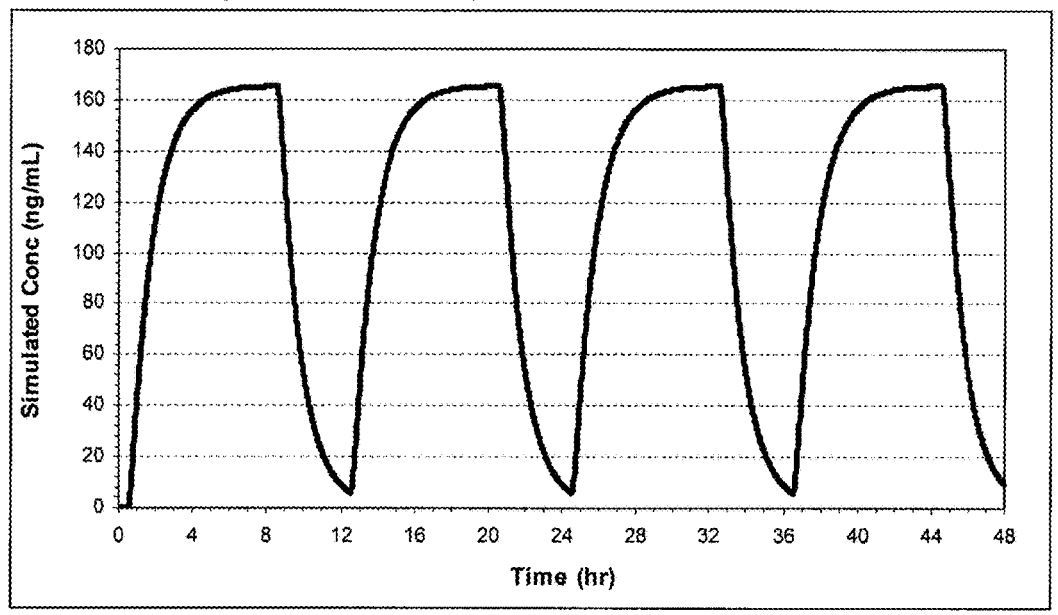
Figure 5:
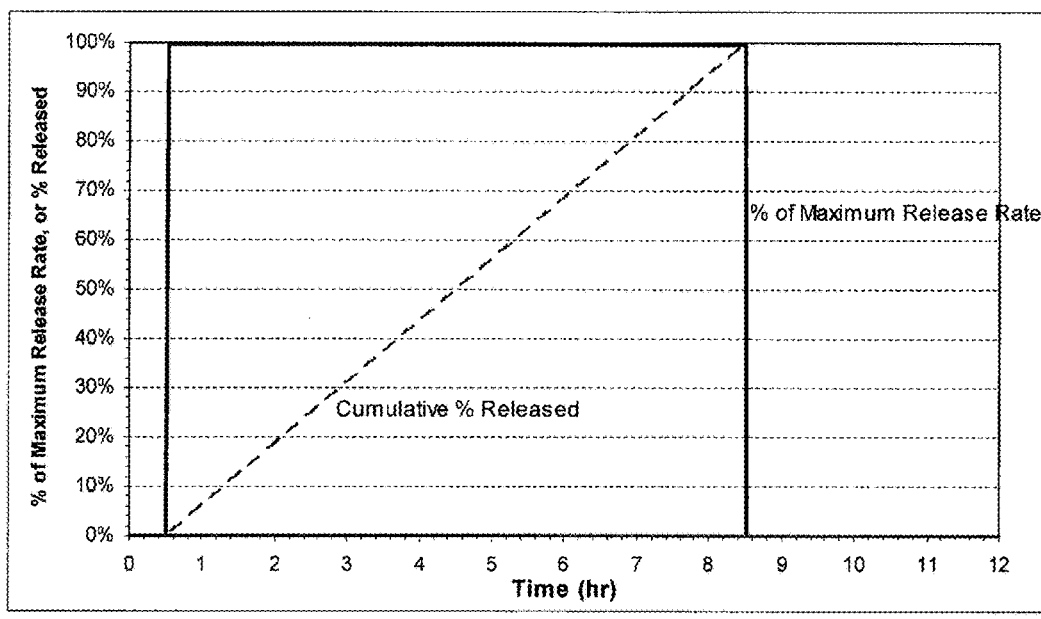
Figure 6:
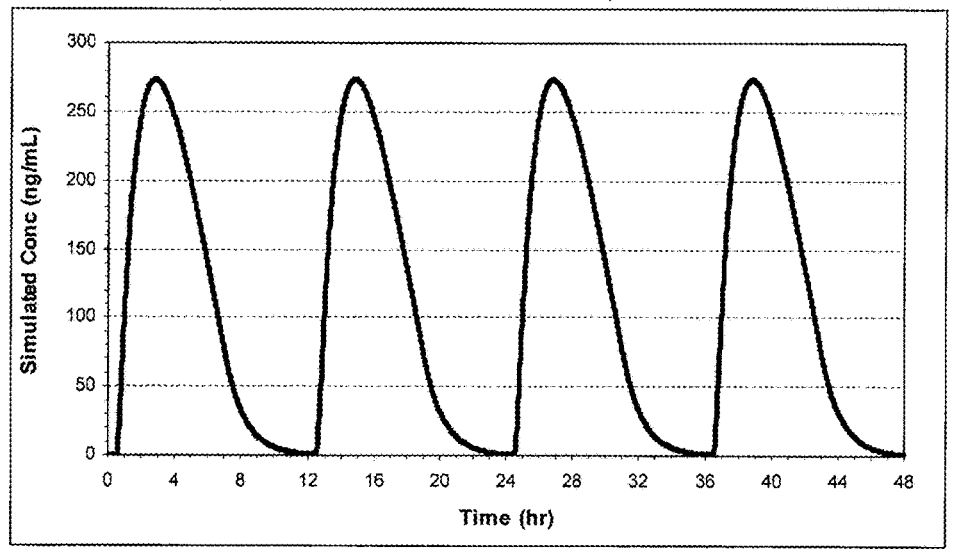
Figure 6:
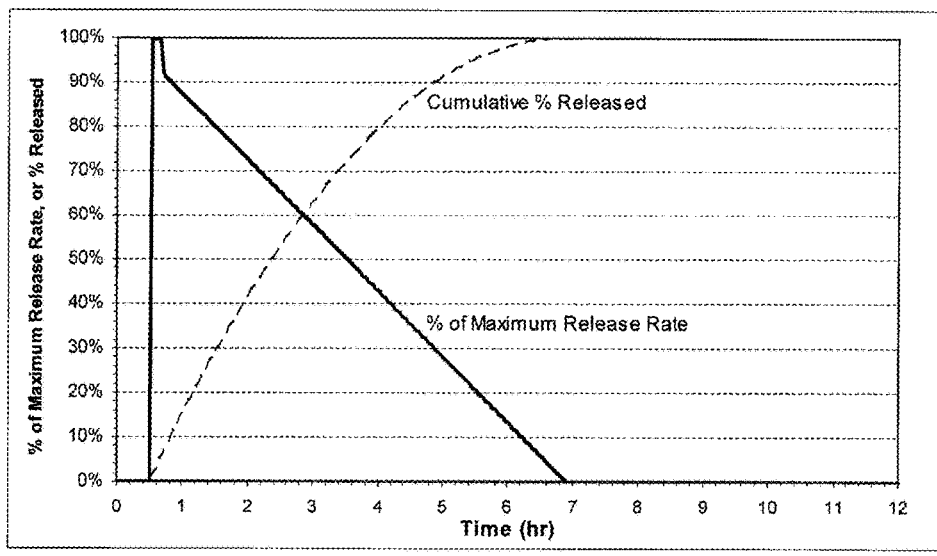
Figure 7:
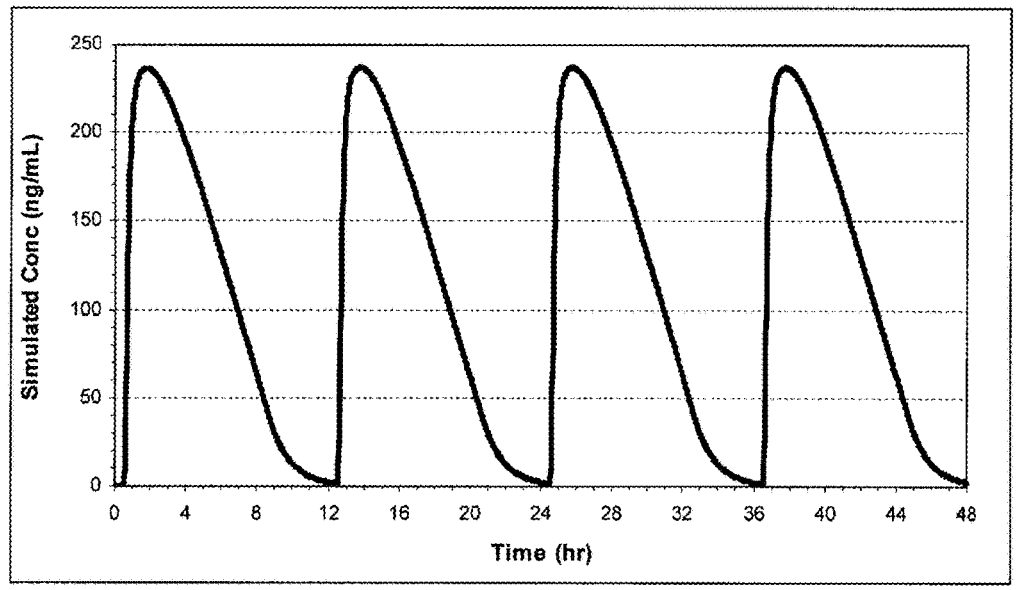
Figure 7:
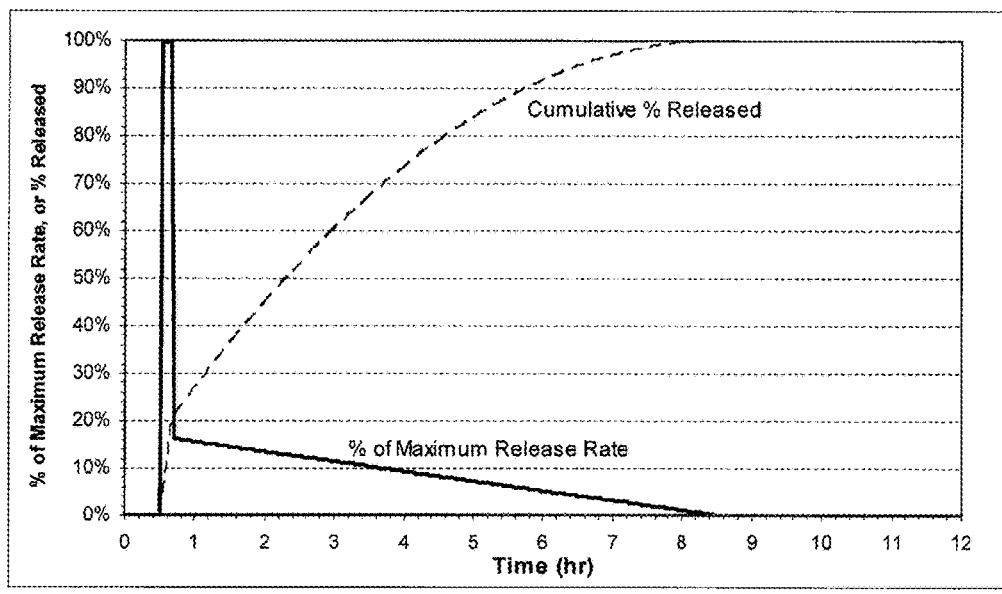
Figure 8:
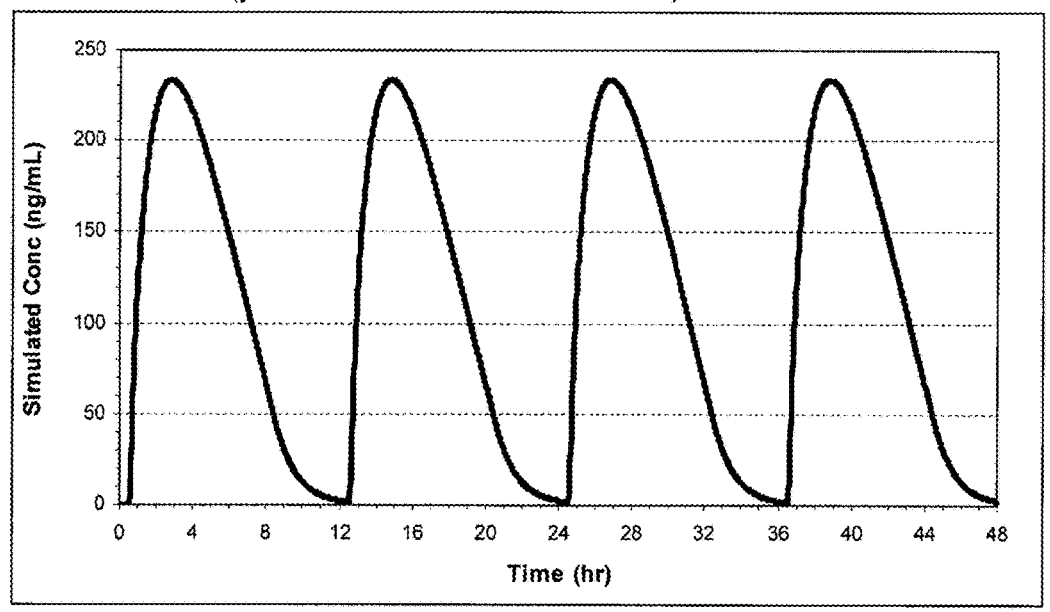
Figure 8:
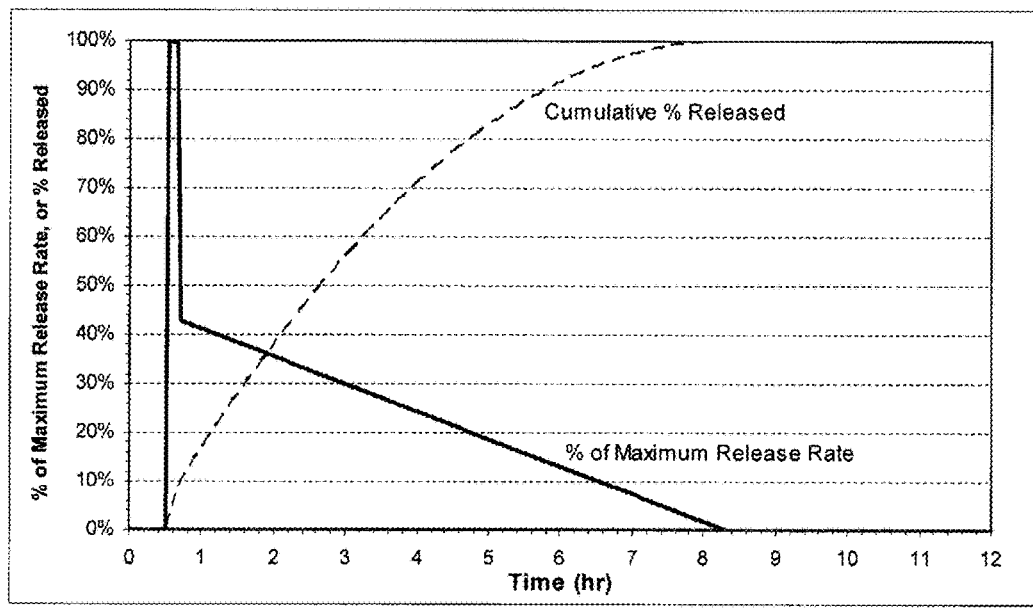
Figure 9:
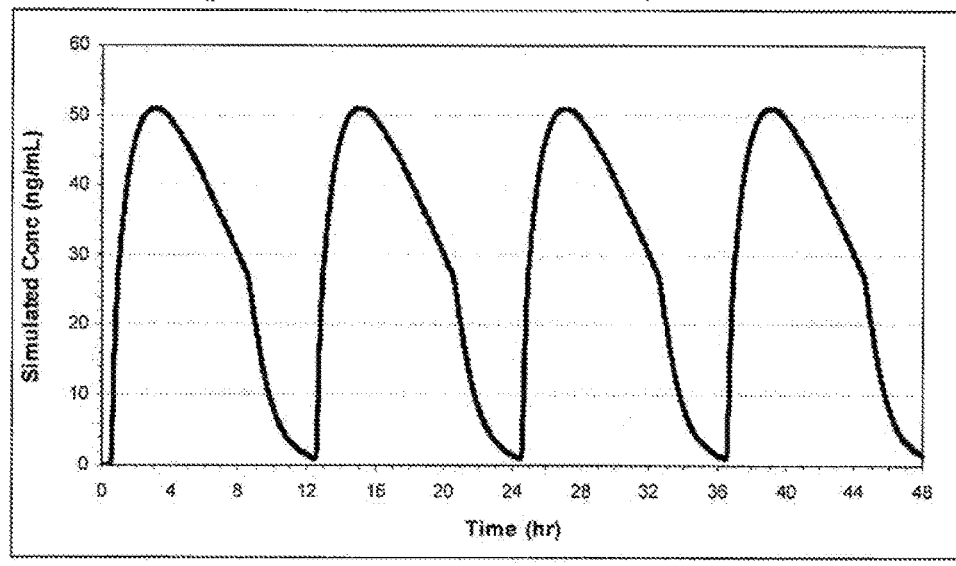
Figure 9:
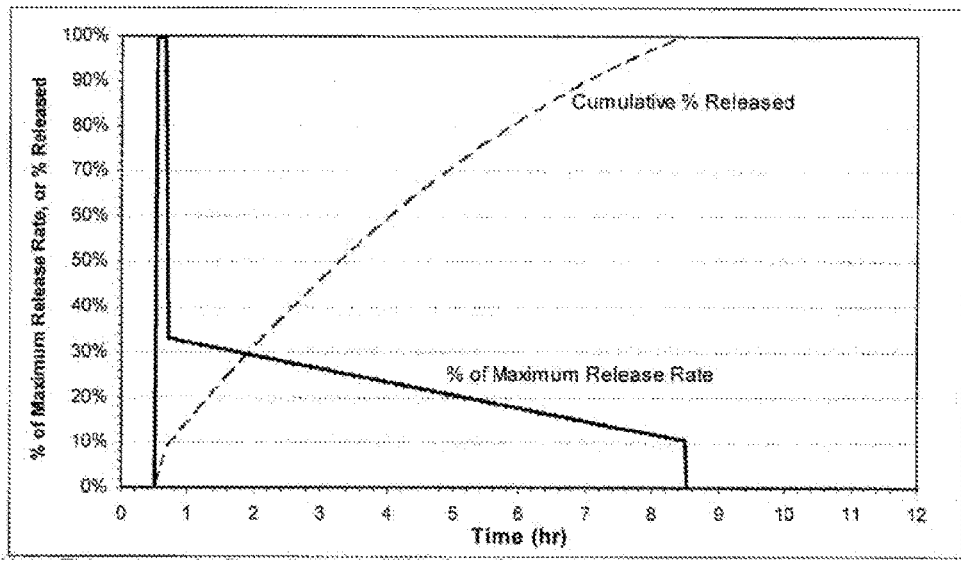
Figure 10:
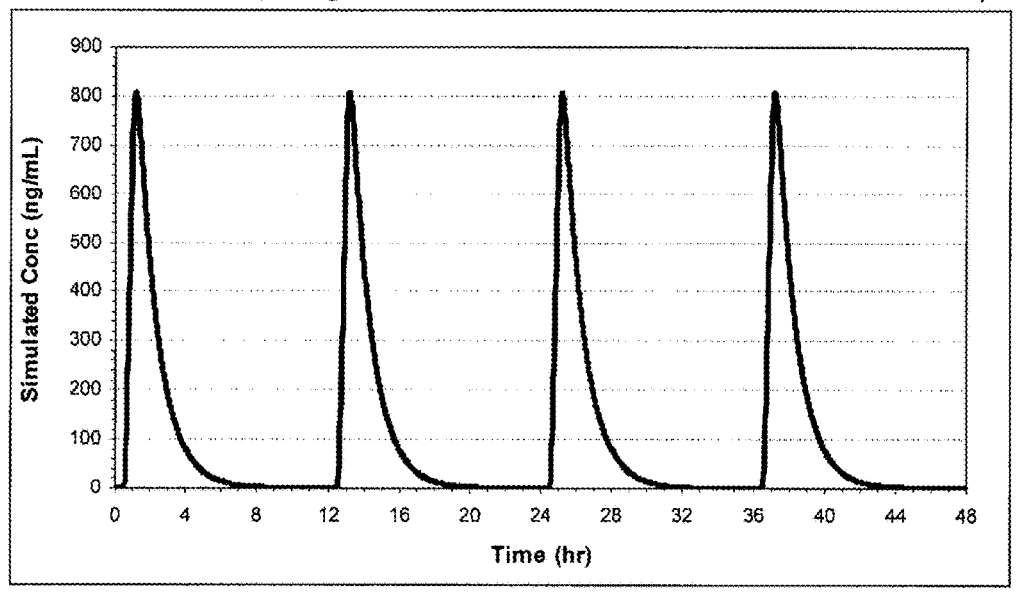
Figure 10:
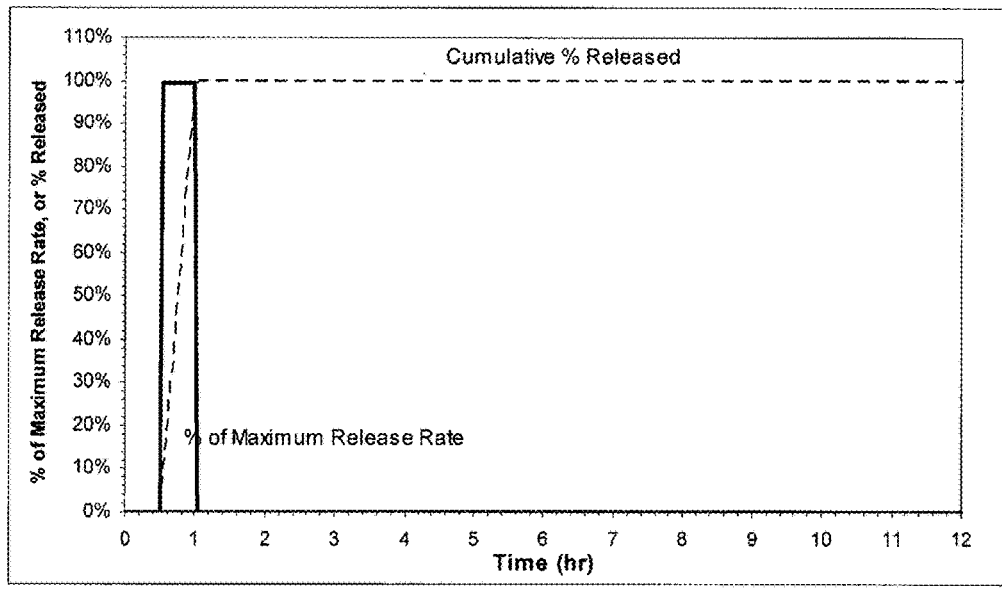

The invention features physiologically acceptable compositions of nitrite, such as inorganic nitrite, and methods by which the compositions can be administered to a patient diagnosed as having, for example, a chronic tissue ischemic disorder.

Nitrite

Inorganic Nitrite

The pharmaceutically acceptable compositions of the invention include inorganic nitrite, e.g., a salt or ester of nitrous acid ($HNO_2$), or a pharmaceutically acceptable salt thereof. Nitrite salts can include, without limitation, salts of alkali metals, e.g., sodium, potassium; salts of alkaline earth metals, e.g., calcium, magnesium, and barium; and salts of organic bases, e.g., amine bases and inorganic bases. Compounds of the invention also include all isotopes of atoms occurring in the intermediate or final compounds. Isotopes include those atoms having the same atomic number but different mass numbers. For example, isotopes of hydrogen include tritium and deuterium. The term "compound," as used herein with respect to any inorganic nitrite or pharmaceutically acceptable salt, solvate, or prodrug thereof. All compounds, and pharmaceutical acceptable salts thereof, are also meant to include solvated (e.g., hydrated) forms. Nitrite has the chemical formula $NO_2$ and may exist as an ion in water. Sodium nitrite has the chemical formula $NaNO_2$ and typically dissolves in water to form the sodium ion $Na^+$ and the nitrite ion $NO_2^-$. It will further be understood that the present invention encompasses all such solvated forms (e.g., hydrates) of the nitrite compounds. Exemplary nitrite compounds are described in WO 2008/105730, which is hereby incorporated by reference.

In addition to sodium nitrite, representative inorganic nitrite compounds include: ammonium nitrite ($NH_4NO_2$), barium nitrite ($Ba(NO_2)_2$; e.g., anhydrous barium nitrite or barium nitrite monohydrate), calcium nitrite ($Ca(NO_2)_2$; e.g., anhydrous calcium nitrite or calcium nitrite monohydrate), cesium nitrite ($CsNO_2$), cobalt(II) nitrite ($Co(NO_2)_2$), cobalt(III) potassium nitrite ($CoK_3(NO_2)_6$; e.g., cobalt(III) potassium nitrite sesquihydrate), lithium nitrite ($LiNO_2$; e.g., anhydrous lithium nitrite or lithium nitrite monohydrate), magnesium nitrite ($MgNO_2$; e.g., magnesium nitrite trihydrate), postassium nitrite ($KNO_2$), rubidium nitrite ($RbNO_2$), silver(I) nitrite ($AgNO_2$), strontium nitrite ($Sr(NO_2)_2$), and zinc nitrite ($Zn(NO_2)_2$).

The compounds of the present invention can be prepared in a variety of ways known to one of ordinary skill in the art of chemical synthesis. Methods for preparing nitrite salts are well known in the art and a wide range of precursors and nitrite salts are readily available commercially. Nitrites of the alkali and alkaline earth metals can be synthesized by reacting a mixture of nitrogen monoxide (NO) and nitrogen dioxide ($NO_2$) with a corresponding metal hydroxide solution, as well as through the thermal decomposition of the corresponding nitrate. Other nitrites are available through the reduction of the corresponding nitrates.

The present compounds can be prepared from readily available starting materials using the methods and procedures known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Suitable pharmaceutically acceptable salts include, for example, sodium nitrite, potassium nitrite, or calcium nitrite. Still other exemplary salts are found in Remington's Pharmaceutical Sciences, 17th ed., Mack Publishing Company, Easton, Pa., 1985, p. 1418, Berge et al., *J. Pharmaceutical Sciences* 66:1-19, 1977 and *Pharmaceutical Salts: Properties, Selection, and Use*, (Eds. P. H. Stahl and C. G. Wermuth), Wiley-VCH, 2008, each of which is incorporated herein by reference in its entirety.

Pharmaceutical Compositions

The pharmaceutically acceptable compositions of the invention include inorganic nitrite, e.g., a salt of nitrous acid ($HNO_2$) such as $NaNO_2$, or a pharmaceutically acceptable salt, solvate, or prodrug thereof. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, such as preservatives.

The therapeutic agents of the invention can be administered alone, or in a mixture, in the presence of a pharmaceutically acceptable excipient or carrier. The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 21$^{st}$ Ed., Gennaro, Ed., Lippencott Williams & Wilkins (2005), a well-known reference text in this field, and in the USP/NF (United States Pharmacopeia and the National Formulary). In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyirolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. Other exemplary excipients are described in *Handbook of Pharmaceutical Excipients*, 6$^{th}$ Edition, Rowe et al., Eds., Pharmaceutical Press (2009).

The pharmaceutical composition can include nitrate salts, or prodrugs thereof, or other therapeutic agents. Exemplary nitrate salts are described in WO 2008/105730. Exemplary therapeutic agents that may be included in the compositions described herein are cardiovascular therapeutics (e.g., anti-thrombotics (e.g. dipyridamole, clopidogrel, and the like), anti-hypertensives (e.g., $Ca^{++}$ channel blockers, AT-2 blockers, ACE inhibitors, and the like), anti-cholesterols (e.g., statins, fibrates, and the like), and thiazolidinedione therapeutics.

The pharmaceutical compositions can be formulated so as to provide immediate, extended, or delayed release of the active ingredient after administration to the patient by employing procedures known in the art.

The compositions can be formulated in a unit dosage form, each dosage containing, e.g., 0.1-500 mg of the active ingredient. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or, from about 100 mg to about 250 mg of the active ingredient. For preparing solid compositions such as tablets, the principal active ingredient is mixed with one or more pharmaceutical excipients to form a solid bulk formulation composition containing a homogeneous mixture of a compound of the present invention. When referring to these bulk formulation compositions as homogeneous, the active ingredient is typically dispersed evenly throughout the composition so that the composition can be readily subdivided into equally effective unit dosage forms such as tablets and capsules. This solid bulk formulation is then subdivided into unit dosage forms of the type described above containing from, for example, 0.1 to about 500 mg of the active ingredient of the present invention.

Compositions for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration vs time profile. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Coatings

The pharmaceutical compositions formulated for oral delivery, such as tablets or capsules of the present invention can be coated or otherwise compounded to provide a dosage form affording the advantage of delayed or extended release. The coating may be adapted to release the active drug substance in a predetermined pattern (e.g., in order to achieve a controlled release formulation) or it may be adapted not to release the active drug substance until after passage of the stomach, e.g., by use of an enteric coating (e.g., polymers that are pH-sensitive ("pH controlled release"), polymers with a slow or pH-dependent rate of swelling, dissolution or erosion ("time-controlled release"), polymers that are degraded by enzymes ("enzyme-controlled release" or "biodegradable release") and polymers that form firm layers that are destroyed by an increase in pressure ("pressure-controlled release")). Exemplary enteric coatings that can be used in the pharmaceutical compositions described herein include sugar coatings, film coatings (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or coatings based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

For example, the tablet or capsule can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

When an enteric coating is used, desirably, a substantial amount of the drug is released in the lower gastrointestinal tract.

In addition to coatings that effect delayed or extended release, the solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, vols. 5 and 6, Eds. Swarbrick and Boyland, 2000.

Formulations for Colonic Drug Release

In some embodiments, colon-targeted drug delivery systems can be used. Exemplary approaches include, but are not limited to:

(a) covalent linkage of the drug with the carrier to form a prodrug that is stable in the stomach and small intestine and releases the drug in the large intestine upon enzymatic transformation by the intestinal microflora; examples of these prodrugs include azo-conjugates, cyclodextrin-conjugates, glycoside-conjugates, glucuronate conjugates, dextran-conjugates, polypeptide and polymeric conjugates;

(b) approaches to deliver intact molecule to the colon, such as coating with pH-sensitive polymers to release the drug at neutral to alkaline pH, or coating with biodegradable polymers which release the drug upon degradation by the bacteria in the colon;

(c) embedding the drug in biodegradable matrices and hydrogels which release the drug in response to the pH or biodegradation;

(d) time released systems where once the multicoated formulation passes the stomach, the drug is released after a lag time of 3-5 hrs which is equivalent to the transit time of the small intestine;

(e) using redox-sensitive polymers where a combination of azo and disulfide polymers, provide drug release in response to the redox potential of the colon;

(f) using bioadhesive polymers which selectively adhere to the colonic mucosa slowly releasing the drug; and (g) osmotic controlled drug delivery where the drug is released through semi-permeable membrane due to osmotic pressure.

Parenteral Administration

Within the scope of the present invention are also parenteral depot systems from biodegradable polymers. These systems are injected or implanted into the muscle or subcutaneous tissue and release the incorporated drug over extended periods of time, ranging from several days to several months. Both the characteristics of the polymer and the structure of the device can control the release kinetics which can be either continuous or pulsatile. Polymer-based parenteral depot systems can be classified as implants or microparticles. The former are cylindrical devices injected into the subcutaneous tissue whereas the latter are defined as spherical particles in the range of 10-100 µm. Extrusion, compression or injection molding are used to manufacture implants whereas for microparticles, the phase separation method, the spray-drying technique and the water-in-oil-in-water emulsion techniques are frequently employed. The most commonly used biodegradable polymers to form microparticles are polyesters from lactic and/or glycolic acid, i.g. poly(glycolic acid) and poly(L-lactic acid) (PLG/PLA microspheres). Of particular interest are in situ forming depot systems, such as thermoplastic pastes and gelling systems formed by solidification, by cooling, or due to the sol-gel transition, cross-linking systems and organogels formed by amphiphilic lipids. Examples of thermosensitive polymers used in the aforementioned systems include, N-isopropylacrylamide, poloxamers (ethylene oxide and propylene oxide block copolymers, such as poloxamer 188 and 407), poly(N-vinyl caprolactam), poly(siloethylene glycol), polyphosphazenes derivatives and PLGA-PEG-PLGA.

Dosing Regimes

The present methods for treating chronic tissue ischemia are carried out by administering an inorganic nitrite for a time and in an amount sufficient to result in the growth of new blood vessels in the ischemic tissue.

The amount and frequency of administration of the compositions can vary depending on, for example, what is being administered, the state of the patient, and the manner of administration. In therapeutic applications, compositions can be administered to a patient suffering from chronic tissue ischemia in an amount sufficient to relieve or least partially relieve the symptoms of chronic tissue ischemia and its complications. The dosage is likely to depend on such variables as the type and extent of progression of the chronic tissue ischemia, the severity of the chronic tissue ischemia, the age, weight and general condition of the particular patient, the relative biological efficacy of the composition selected, formulation of the excipient, the route of administration, and the judgment of the attending clinician. Effective doses can be extrapolated from dose-response curves derived from in vitro or animal model test system. An effective dose is a dose that produces a desirable clinical outcome by, for example, improving a sign or symptom of chronic tissue ischemia or slowing its progression.

The amount of inorganic nitrite per dose can vary. For example, a subject can receive from about 0.1 µg/kg to about 10,000 µg/kg. Generally, the nitrite is administered in an amount such that the peak plasma concentration ranges from 150 nM-250 µM. Exemplary dosage amounts can fall between 0.1-5000 µg/kg, 100-1500 µg/kg, 100-350 µg/kg, 340-750 µg/kg, or 750-1000 µg/kg. Exemplary dosages can 0.25, 0.5, 0.75, or 1° mg/kg. Exemplary peak plasma concentrations can range from 0.05-10 µM, 0.1-10 µM, 0.1-5.0 µM, or 0.1-1 µM. The peak plasma concentrations may be maintained for 6-14 hours, e.g., for 6-12 or 6-10 hours.

The frequency of treatment may also vary. The subject can be treated one or more times per day (e.g., once, twice, three, four or more times) or every so-many hours (e.g., about every 2, 4, 6, 8, 12, or 24 hours). Preferably, the pharmaceutical composition is administered 1 or 2 times per 24 hours. The time course of treatment may be of varying duration, e.g., for two, three, four, five, six, seven, eight, nine, ten or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Kits

Any of the pharmaceutical compositions of the invention described herein can be used together with a set of instructions, i.e., to form a kit. The kit may include instructions for use of the pharmaceutical compositions as a therapy as described herein. For example, the instructions may provide dosing and therapeutic regimes for use of the compounds of the invention to reduce chronic tissue ischemia.

Methods of Treatment

Nitrite as Nutritional Supplementation

Plasma nitrite levels have been shown to be inversely correlated to cardiovascular risk factors, with subjects having the greatest number of risk factors, having the lowest level of plasma nitrites (Kleinbongard et al., *Free Radical Biology & Medicine* 40:295-302, 2006). In normal subjects, exercise results in a release of stored nitrite to the plasma, increasing plasma nitrite levels; however, in diabetic and PAD patients, exercise does not increase the level of plasma nitrite and in fact, leads to a further decrease in circulating nitrite levels (Allen et al, *Nitric Oxide* 20:231-237, 2009). Thus, a nutritional supplementation of nitrite might be effective in overcoming these deficits in plasma nitrite levels in cardiovascular and vascular disorders and given the relationship of nitrite to nitric oxide, the deficits in nitric oxide found in these diseases or due to dietary deficiencies in nitrite.

The present invention provides nutritional compositions of nitrite, e.g., inorganic nitrite, or a pharmaceutically acceptable prodrug thereof, for both prophylactic and therapeutic nutritional supplementation, specifically in cardiovascular, metabolic, inflammatory or vascular diseases. Specifically, the present invention relates to novel compositions of nitrite, e.g., inorganic nitrite, or a pharmaceutically acceptable prodrug thereof, that can be used to supplement the nutritional deficiencies observed in patients with diabetes, peripheral artery disease, chronic infections, acute infections, congestive heart failure, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, stem cell diseases, and/or dietary restrictions. In addition, the compositions may be used to treat the nutritional deficiencies of patients suffering from a disease state that results in decreased plasma nitrite or nitric oxide levels.

Inflammatory Diseases

The pharmaceutical compositions and methods described herein can be used to treat innate and acquired inflammatory diseases. The inflammatory diseases encompassed by the methods of this invention can stem from a wide range of medical conditions that cause inflammation. One type of inflammatory diseases which can be treated by the compositions and methods described in this invention are immuno-inflammatory diseases. Examples of immuno-inflammatory diseases include rheumatoid arthritis, juvenile rheumatoid arthritis, osteoarthritis, transplant rejection, sepsis, acute respiratory distress syndrome, asthma, and cancer. Another type of inflammatory diseases which can be treated by the composition and methods described in this invention are the autoimmune diseases. Examples of autoimmune diseases include such conditions as multiple sclerosis, psoriasis, inflammatory bowel disease, glomerulonephritis, lupus, uveitis, and chronic hepatitis. Other inflammatory diseases can also be treated by the compositions and methods described in this invention, including such conditions caused by trauma, oxidative stress, cell death, irradiation damage, ischemia, reperfusion, cancer, transplant rejection, and viral infection.

Tissue Regeneration

The pharmaceutical compositions and methods described herein can be used to stimulate tissue regeneration, e.g., following damage to a tissue or organ caused by such conditions as trauma, scarring, abnormal protein deposition, amyloidoses, ischemia or diabetes, infections, or surgical procedures; congenital malformations such as hernias, cardiac defects and gastrointestinal defects that result in damage to the tissue.

Chronic Tissue Ischemia

Chronic tissue ischemia is associated with a wide range of medical conditions that result in partial, substantially complete or complete reduction of blood flow to a body part or tissue comprising a body part and may be the result of disease, injury, or of an unknown cause, and may be influenced by one's genetic constitution. Regardless of the medical condition leading to chronic tissue ischemia, a patient who has chronic tissue ischemia is a candidate for treatment with the pharmaceutically acceptable compositions comprising inorganic nitrite described herein. Treatment can completely or partially abolish some or all of the signs and symptoms of chronic tissue ischemia, decrease the severity of the symptoms, delay their onset, or lessen the progression or severity of subsequently developed symptoms.

New Blood Vessel Growth

As described further below, the compositions of the invention are administered for a time and in an amount sufficient to result in the growth of new blood vessels in the ischemic tissue. We may use the terms "new blood vessel growth," "new blood vessel formation" and "new blood vessel development" interchangeably. New blood vessel growth refers all phases of the process of blood vessel formation, including the initial signaling events, cellular recruitment of endothelial cells, the formation and enlargement of new vessels and connection of new vessels with pre-existing vessels. The new blood vessel growth may stem from any process that results in revascularization or neovascularization of the ischemic tissue, for example, angiogenesis, or arteriogenesis, or a combination of angiogenesis and arteriogenesis. The term vasculogenesis typically is used to describe the embryonic development of blood vessels from angioblasts. Angiogenesis is generally understood to be a post-natal physiologic process required for would healing. Angiogenesis generally encompasses the formation of new capillaries or capillary branches by sprouting, budding and intussusception from pr-existent capillaries. Arteriogenesis i.e., the growth of preexisting arteriolar connections into true collateral arteries, is generally understood to encompass the formation of mature arteries from pre-existent interconnecting arterioles after an arterial occlusion. It shares some features with angiogenesis, but the pathways leading to it can differ, as do the final results: arteriogenesis is potentially able to fully replace an occluded artery whereas angiogenesis typically cannot. Increasing the number of capillaries within the ischemic region cannot increase blood flow when the limiting structure lies upstream of the new capillaries; formation of new collateral vessels that divert blood flow around the site of a blockage. In addition, the structures produced by angiogenesis and arteriogenesis differ in their cellular composition. Capillaries are tubes formed by endothelial cells which are supported by vascular pericytes. Arteries and veins are tubes that consist of multiple layers: the intima, which is composed of endothelial cells, pericytes, and a basement membrane; the media, which is composed principally of smooth muscle cells and their extracellular matrix; and, in the largest vessels, the adventitia, which is composed principally of fibroblasts and their extracellular matrix.

Chronic Tissue Ischemia

Methods of the invention are applicable to any of a wide range of medical conditions which have as their underlying feature a persistent reduction of or partial or complete blockage of blood flow to a tissue or organ. Thus, the methods are applicable to treatment of chronic tissue ischemia associated with a disorder, with a trauma or an environmental stress. The reduction in blood flow to a tissue can be, for example, the result of a progressive blockage of an artery due to hardening and/or loss of elasticity due to an atheromatous plaque or the presence of a clot. Reduction of blood flow to a tissue can also be the result of an environmental insult, for example, a traumatic injury or surgical procedure that interrupts the blood flow to a tissue or organ. Typically, the oxygen tension of a wound quickly and progressively decreases with the development of varying degrees of hypoxia throughout the wound region. Environmental conditions that induce hypoxia are also within the scope of the invention.

Disorders encompassed by the invention include, for example, cardiovascular disease, peripheral artery disease, arteriosclerosis, atherosclerotic cardiovascular disease, myocardial infarction, critical limb ischemic disease, stroke, acute coronary syndrome, intermittent claudication, diabetes, including type 1 and type 2 diabetes, skin ulcers, peripheral neuropathy, inflammatory bowel disease, ulcerative colitis, Crohn's disease, intestinal ischemia, and chronic mesenteric ischemia. The methods of the invention are also applicable to chronic tissue ischemia associated with a trauma, for example, a traumatic injury such as a wound, laceration, burn, contusion, bone fracture or chronic infection. Also encompassed by the invention are tissue injuries sustained as part of any surgical procedure, for example, endarterectomy. Procedures involving tissue or organ transplantation are within the scope of the invention. Examples include vascular bypass grafts, heart, liver, lung, pancreatic islet cell transplantation as well as transplantation of tissues generated ex vivo for implantation in a host. The methods of the invention are also useful for treating a chronic ischemic condition brought about by exposure to an environmental insult, for example, chronic exposure to hypoxic conditions e.g., high altitude, or sustained aerobic exertion.

The methods provided herein are applicable to any of a wide range of tissue types including, for example, muscle, smooth muscle, skeletal muscle, cardiac muscle, neuronal tissue, skin, mesechymal tissue, connective tissue, gastrointestinal tissue or bone. Soft tissue, such as epithelial tissue, e.g., simple squamous epithelia, stratified squamous epithelia, cuboidal epithelia, or columnar epithelia, loose connective tissue (also known as areolar connective tissue), fibrous connective tissue, such as tendons, which attach muscles to bone, and ligaments, which join bones together at the joints.

Thus, for example symptoms of chronic tissue ischemia in peripheral artery disease (PAD), a form of peripheral vascular disease in which there is partial or total blockage of an artery, usually due to atherosclerosis in a vessel or vessels leading to a leg or arm, can include intermittent claudication, that is, fatigue, cramping, and pain in the hip, buttock, thigh, knee, shin, or upper foot during exertion that goes away with rest, claudication during rest, numbness, tingling, or coldness in the lower legs or feet, neuropathy, or defective tissue wound healing. PAD in the lower limb is often associated with diabetes, particularly type 2 diabetes. Arm artery disease is usually not due to atherosclerosis but to other conditions such as an autoimmune disease, a blood clot, radiation therapy, Raynaud's disease, repetitive motion, and trauma. Common symptoms when the arm is in motion include discomfort, heaviness, tiredness, cramping and finger pain. PAD can be diagnosed by performing one or more diagnostic tests including, for example, an ankle brachial index (ABI) test, angiography, ultrasound, or MRI analysis.

Myocardial ischemia can have few or no symptoms, although typically, it is associated with symptoms such as angina, pain, fatigue elevated blood pressure. Diagnostic tests for myocardial ischemia include: angiography, resting, exercise, or ambulatory electrocardiograms; scintigraphic studies (radioactive heart scans); echocardiography; coronary angiography; and, rarely, positron emission tomography.

The method of the invention can also be used in conjunction with other remedies known in the art that are used to treat chronic tissue ischemia including, drug therapy, surgery, anti-inflammatory agents, antibodies, exercise, or lifestyle changes. The choice of specific treatment may vary and will depend upon the severity of the chronic tissue ischemia, the subject's general health and the judgment of the attending clinician.

The present compositions can also be formulated in combination with one or more additional active ingredients, which can include any pharmaceutical agent such antihypertensives, anti-diabetic agents, statins, anti-platelet agents (clopidogrel and cilostazol), antibodies, immune suppressants, anti-inflammatory agents, antibiotics, chemotherapeutics, and the like. In some embodiments, the composition also includes an inorganic nitrate; in other embodiments, the composition excludes inorganic nitrates. For example, the present composition can include inorganic nitrite and nitrates in a ratio that is between 1-5 to 1-100 nitrite:nitrate, e.g., 1-5, 1-10, 1-30, 1-50, 1-70, or 1-100 nitrite:nitrate.

EXAMPLES

Controlled Release Pharmaceutical Formulations

Exemplary formulations for oral administration include tablet and capsule formulations. For example, the powdered components described for a tablet formulation can be used to prepare a capsule formulation, a suitable capsule size depending on the dose of the active and density of the fill, such as size 1, 0, or 00 capsules. In some embodiments, the table or capsule may not have an enteric coating. In other embodiments, the pharmaceutical compositions of the invention can be formulated for controlled release of nitrite ion. If a capsule is described as coated, the coating can be applied to the capsule after filling. Capsule formulations can optionally employ self-locking capsule shells (e.g., Coni-Snap®, Posilok®, Snap-Fit®, or the like) for ease of handling during the coating process.

The exemplary compositions include between 0.5-4.0 mmol of total nitrite ion; specifically, between 1.8-3.6 mmol of $NaNO_2$. The compositions can include any prodrug of nitrite thereof, e.g., 125-250 mg of $NaNO_2$, 154-308 mg of $KNO_2$, or 201-402 mg of arginine nitrite. The amount of nitrite ion used in the pharmaceutical compositions can be varied as described herein. For example, the formulations can also include any of the excipients described herein, preferably an alkanizing agent (e.g., sodium bicarbonate or calcium carbonate), a glidant (e.g., fumed silica), a lubricant (a fatty acid salt (e.g., magnesium stearate), a pure solid fatty acid, or solid polyethylene glycol), or a bulking agent with good flow properties (e.g., silicified microcrystalline cellulose (Prosolvo SMCC90)). The compositions can also include any of the excipients described for use in compositions that are formulated for enteric release, e.g., in enteric formulations. Formulations can also include rate-controlling polymer coatings (e.g., ethyl cellulose, cellulose acetate, cellulose acetate butyrate, cellulose triacetate and the like, which can be combined with PEG-4000). If desired, the amount of PEG-4000 used can be varied in order to generate aqueous pores in the coat through which the sodium nitrite can diffuse. Enteric polymer coatings can also be used, and exemplary polymers include cellulose acetate phthalate (CAP), cellulose trimellitate, hydroxypropylmethylcellulose acetate succinate, Eudragit® L or S, or the like Where a polymer coating is used, the formulation can also include a plasticizer (e.g., triethylcitrate, triacetin, acetyl monoglycerides, or the like). The total enteric coat (polymer+plasticizer) can be added in an amount that, for example, results in a 10% weight gain.

The production and testing of several tablet and pellet formulations for the controlled release of nitrate is described below.

Tablet Preparation Procedures

All solid components, including sodium nitrite, were weighed to produce tablets with the desired weight ratios of components. Enough powder blend was prepared to prepare 4-5 tablets. The powdered components were thoroughly mixed before compressing into tablets. For tablets containing a waxy component (i.e. Castorwax®), sodium nitrite and other components were dispersed in molten wax and the mixture solidified while mixing to maintain a homogeneous blend. After solidifying, the mixture was ground to powder for further mixing, if required. Mixing of all powdered components was accomplished with a mortar and pestle.

The tablets were compressed on a Carver® Press with a ½" (1.27 cm) punch and die. A force of 5000 lbs was applied for 30 seconds to obtain tablets for release testing.

The tablet dimensions were:
580 mg tablets: 1.27 cm dia.×0.38 cm thickness (½"×⅛") or
480 mg tablets: 1.27 cm dia.×0.32 cm thickness (½"×⅛")

Tablet thicknesses were dependent on the total weight of powdered components and the nature of the excipients employed. Thus, the thicknesses disclosed varied between 10-15%, depending on the mixture being compressed.

The tablets were carefully pushed from the die after compression and stored in a desiccator until dissolution testing. Some tablets were coated with controlled release or enteric coating materials to alter their release profiles.

Pellet Preparation Procedures

Small pellets containing 5 mg of sodium nitrite were prepared according to the following procedure for animal testing (oral administration to rabbits). All solid components, including sodium nitrite, were weighed to produce pellets with the desired weight ratios of components. Enough powder blend was prepared to prepare 40-50 pellets.

The powdered components were sieved (150-250 microns) and thoroughly mixed by geometric dilution before compressing into pellets. The pellets were compressed with a Parr Model 2811 pellet press with a 3 mm punch-and-die. The pellet press operated with manual compression and did not allow control of the applied force but did produce cohesive pellets for all formulations. The pellets weighed 23-35 mg depending on the formulation employed. One pellet batch was manually coated with an ethylcellulose/triacetin coating (4/1) which was 11-15% of the pellet weight.

The pellet dimensions were: 3 mm dia.×5-7 mm thickness. Pellet thicknesses were dependent on the total weight of powdered components and the nature of the excipients employed. Thus, the thicknesses disclosed varied about 50% depending on the mixture being compressed.

The pellets were carefully pushed from the die after compression and stored in a desiccator until shipment for animal testing. One pellet batch was coated with a controlled release coating to alter its release profile. The coating procedure is described separately below. The Castorwax pellets were compressed twice. The first compression was at ambient temperature; the second compression was in the 3 mm die after heating the die to 50-60° C. in an oven. The second compression induced better flow of the Castorwax around the sodium nitrite and sodium acetate particles.

Tablet/Pellet Coating Procedure

Sodium nitrite tablets were coated manually by carefully dropping a measured volume of coating solution on to the tablet and carefully spreading it on the surfaces and edge of the tablet. After solvent evaporation, the process was repeated multiple times until an adequate amount of coating was applied. For pellets and some tablet batches, a dip coating process was employed which involved carefully dipping the pellet/tablet into coating solution and letting it air dry while holding it with forceps. The dipping process was repeated until an adequate amount of coating was applied.

The coatings employed were ethylcellulose (EC) with triacetin as a plasticizer and cellulose acetate phthalate (CAP, Cellacefate, NF). Various ratios of EC and triacetin were employed to obtain coats with different brittleness and different permeabilities to water and sodium nitrite. EC/triacetin was applied to tablets or pellets from solutions that contained chloroform, methylene chlorideor 95% ethanol. CAP was employed as an enteric coating material which was applied to tablets from a dioxane solution. Other coating solvents gave CAP coated tablets which did not withstand simulated gastric fluid for two hours without disintegrating.

Tablet Components

Sodium nitrite, Certified ACS Reagent, crystalline, Fisher Scientific, Lot #080939A
Polyox® Coagulant, Blend #C-289, 5 million MW, N.F. Grade, Union Carbide,
Polyox® WSR 303, 7 million MW, N.F. Grade, Colorcon
Avicel® PH-302, microcrystalline cellulose, FMC Corporation, Lot #Q939C
Ethocel®, ethylcellulose, Standard 100 premium, Colorcon
Castorwax®, NF, hydrogenated castor oil, CASCHEM, Lot #00121431
Methocel® K100M, hydroxypropyl methylcellulose, premium CR grade, Colorcon Klucel® HXAF Pharm., hydroxypropylcellulose, 1.15 million MW, Aqualon Division, Hercules, Inc.
Klucel® MF Pharm., hydroxypropylcellulose, 850,000 MW, Aqualon Division, Hercules, Inc.
Sodium Chloride, Certified ACS Reagent, Fisher Scientific
Sodium Acetate Trihydrate, ACS Reagent, Fisher Scientific Release Testing Procedure for Tablets The USP paddle method was employed at 50 RPM stirring for all nitrite release testing. A Vankel® USP 6-station dissolution apparatus was used. A volume of 500 mL distilled water at 37° C. was used as the release medium in each release vessel. Tablet release studies were conducted in duplicate or triplicate for each formulation tested.

Samples (35 mL) of the release medium were taken from each vessel at regular time intervals (typically ½, 1, 2, 3, 4 hours (or longer). The medium was replenished with 35 mL of distilled water.

At the end of a release run tablets were crushed and allowed to completely release their sodium nitrite content dissolved to determine the total sodium nitrite content in the tablet.

Sodium Nitrite Release Assay

The UV absorbance at 355 nm was measured with a Hewlett-Packard® 8453 diode-array UV-visible spectrophotometer for each release sample in a 10-cm quartz cuvette.

From a previously prepared calibration plot, the concentration of sodium nitrite in each sample was calculated and converted to total amount and percent released for each tablet. The average percent released and standard deviation were calculated for two or three tablets run simultaneously. The average percent released vs. time profiles were plotted for each formulation.

The formulations and release profiles of the tablets and pellets produced by the above methods are set forth in tables 1-7.

TABLE 1

Polyox tablet compositions (mg/tablet)

| Formulation No. | Polyox Coagulant | Polyox WSR 303 | Avicel PH 302 | Sodium nitrite | Ethylcellulose/Triacetin Coating | Total weight |
|---|---|---|---|---|---|---|
| 1 | 200 | 200 | 100 | 80 | — | 580 |
| 9 | 100 | 300 | 100 | 80 | — | 580 |
| 9 C | 100 | 300 | 100 | 80 | 87 (13% w/w) | 667 |
| 14 | 0 | 400 | 0 | 80 | — | 480 |

Formulation 9 C is the same as Formulation 9 except that a 13% coating of ethylcellulose 100/triacetin (⅒) was applied to the tablet from a 95% ethanol solution.

TABLE 2

Polyox tablet release results

| Time (hours) | Formulation 1 | % SD | Formulation 9 | % SD | Formulation 9 C | % SD | Formulation 14 | % SD |
|---|---|---|---|---|---|---|---|---|
| 1 | 41.9% | 7.0% | 29.1% | 8.3% | 8.2% | 0.4% | 33.6% | 8.3% |
| 2 | 54.1% | 5.1% | 47.9% | 9.0% | 20.7% | 0.8% | 59.7% | 11.0% |
| 3 | 66.2% | 3.2% | 64.2% | 8.3% | 34.0% | 2.9% | 75.5% | 9.7% |
| 4 | 76.9% | 2.5% | 75.2% | 6.3% | 48.4% | 5.9% | 86.4% | 6.7% |
| 6 | 91.0% | 0.7% | 91.7% | 3.7% | 74.6% | 9.4% | 93.5% | 2.4% |
| 8 | 100.0% | 0.0% | 100.0% | 0.0% | 100% | 9.0% | 100.0% | 0.0% |

TABLE 3

Pellet compositions for animal studies (mg/pellet)

| Formulation No. | Polyox WSR 303 | Castorwax | Sodium Acetate | Hydroxypropyl-cellulose | Sodium nitrite | Ethylcellulose/Triacetin Coating | Total weight |
|---|---|---|---|---|---|---|---|
| 100A | 25 | — | — | — | 5 | — | 30 |
| 200A | — | 12 | 6 | — | 5 | — | 23 |
| 300A | — | — | — | 25 | 5 | 4-5 (11-15% w/w) | 34-35 |

Formulation 200A was compressed twice. The first compression was at ambient temperature. The second compression was in the 3 mm die after heating the die to 50-600C in an oven. Formulation 300A was dip coated with an ethylcellulose 100/triacetin (4/1) coating solution with 95% ethanol as the solvent.

TABLE 4

Castorwax tablet compositions (mg/tablet)

| Formulation No. | Castorwax | HPMC (K100M) | Sodium Chloride | Sodium Acetate | Sodium nitrite | Ethylcellulose/Triacetin Coating | Total weight |
|---|---|---|---|---|---|---|---|
| 12 | 200 | 200 | — | — | 80 | — | 480 |
| 12 C | 200 | 200 | — | — | 80 | 71 (14.8%) | 551 |
| 13 | 300 | — | 100 | — | 80 | — | 480 |
| 15 | 200 | — | — | 100 | 80 | — | 380 |
| 15 C1 | 200 | — | — | 100 | 80 | 36.5 (9.6%) | 416.5 |
| 15 C2 | 200 | — | — | 100 | 80 | 16 (4.15%) | 396 |

TABLE 5

Castorwax tablet release results

| Time (hours) | Formulation 12 | % SD | Formulation 12 C | % SD | Formulation 13 | % SD | Formulation 15 | % SD | Formulation 15 C1 | % SD | Formulation 15 C2 | % SD |
|---|---|---|---|---|---|---|---|---|---|---|---|---|
| 0.5 | — | — | — | — | — | — | — | — | 0.8% | 0.0% | — | — |
| 1 | 36.0% | 2.9% | 29.1% | — | 17.3% | 1.6% | 58.8% | 0.7% | 2.3% | 0.4% | 2.4% | 0.4% |
| 2 | 53.7% | 3.8% | 46.6% | — | 22.0% | 3.1% | 81.7% | 0.1% | 5.8% | 1.0% | 4.5% | 0.4% |
| 3 | 69.5% | 2.6% | 67.3% | — | 24.3% | 4.0% | 94.8% | 0.8% | 11.5% | 0.3% | 7.9% | 0.6% |
| 4 | 76.6% | 8.6% | 74.1% | — | 27.3% | 3.8% | 100.8% | 0.5% | — | — | 11.8% | 1.4% |
| 6 | 95.8% | 3.9% | 99.5% | — | 32.0% | 4.5% | 100.0% | 0.0% | — | — | 18.2% | 2.2% |
| 8 | 100.0% | 0.0% | 100.0% | — | 35.5% | 4.6% | — | — | 31.9% | 0.7% | 27.5% | 2.9% |
| 24 | — | — | — | — | — | — | — | — | 75.5% | 0.1% | 71.0% | 2.7% |
| 26 | — | — | — | — | 57.1% | 3.0% | — | — | — | — | — | — |

Formulation 12 C is the same as Formulation 12 except that a 14.8% coating of ethylcellulose 100/triacetin (1/10) was applied to the tablet from a 95% ethanol solution. Formulations 13, 15, 15 C1 and 15C2 were prepared by mixing sodium nitrite and other components into melted Castorwax. The molten mass was mixed while solidifying and then ground into a powder with a mortar and pestle before compressing into tablets. Formulations 15 C1 and 15 C2 are the same as Formulation 15 except that a 9.6% (15 C1) or a 4.15% (15 C2) coating of ethylcellulose 100/triacetin (4/1) was applied to the tablets from a chloroform.

TABLE 6

Ethylcellulose and HPMC tablet compositions (mg/tablet)

| Formulation No. | Ethylcellulose | HPMC (K100M) | HPMC (K15M) | Avicel PH-302 | HPCMF | Sodium nitrite | Ethylcellulose/Triacetin Coating | Total weight |
|---|---|---|---|---|---|---|---|---|
| 2 | 400 | — | — | — | — | 80 | — | 480 |
| 5 | 200 | 200 | — | — | — | 80 | — | 480 |
| 10 C | — | 200 | — | 200 | — | 80 | 76 (15.8%) | 556 |
| 16 | — | — | 400 | — | — | 80 | — | 480 |
| 17 C | — | — | — | — | 400 | 80 | 41.5 (8.65%) | 521.5 |

TABLE 7

Ethylcellulose and HPMC tablet release results

| Time (hours) | Formulation 2 | % SD | Formulation 5 | % SD | Formulation 10 C | % SD | Formulation 16 | % SD | Formulation 17 C | % SD |
|---|---|---|---|---|---|---|---|---|---|---|
| 0.5 | — | — | — | — | — | — | — | — | — | — |
| 1 | 56.0% | 1.4% | 50.0% | 2.3% | 24.7% | — | 38.2% | 1.1% | 0.8% | 0.7% |
| 2 | 73.8% | 2.3% | 68.8% | 5.3% | 60.6% | — | 53.0% | 1.3% | 1.1% | 1.0% |
| 3 | 84.3% | 2.1% | 81.2% | 5.1% | 79.2% | — | 78.9% | 8.6% | 2.9% | 1.6% |
| 4 | 91.1% | 2.1% | 89.2% | 4.8% | 87.7% | — | 88.2% | 5.4% | 6.7% | 0.9% |

TABLE 7-continued

Ethylcellulose and HPMC tablet release results

| Time (hours) | Formulation 2 | % SD | Formulation 5 | % SD | Formulation 10 C | % SD | Formulation 16 | % SD | Formulation 17 C | % SD |
|---|---|---|---|---|---|---|---|---|---|---|
| 6 | 96.6% | 0.2% | 95.3% | 2.2% | 97.1% | — | 96.3% | 4.1% | 18.0% | 0.5% |
| 8 | 100.0% | 0.0% | 100.0% | 0.0% | 100.0% | — | — | — | 31.6% | 2.4% |
| 24 | — | — | — | — | — | — | — | — | 88.4% | 7.5% |

Formulation 10 C has a 15.8% coating of ethylcellulose 100/triacetin (1/10) applied to the tablet from a 95% ethanol solution. Formulation 2 was prepared by mixing sodium nitrite with powdered ethylcellulose (Ethocel® 100) and compressing the blend into tablets. Formulation 5 was prepared by mixing sodium nitrite, powdered ethylcellulose (Ethocel® 100) and HPMC K100M and compressing the blend into tablets. Formulations 17 C contains hydroxypropylcellulose (Klucel MF) and has a 8.65% coating of ethylcellulose 100/triacetin (4/1) applied from a chloroform solution.

Simulations of Nitrite Plasma Levels from Controlled Release Formulations

Certain of the above formulations were simulated for determination of their nitrite plasma levels. The simulations assume mid-range pharmacokinetic constants and an 80 mg dose. The assumed PK parameters for $NaNO_2$ are: half-life=45 minutes; clearance=60.375 L/hr; oral bioavailability=100% (except for formulation 27, which is 27%); lag time between dosing and reaching a pH where the release can occur=0.5 hours. The simulations are for the first two days of twice daily dosing. A concentration of 69 ng/mL is equivalent to 1 $\mu$M, and 138 ng/mL is 2 $\mu$M. The results are shown in FIGS. 1-10.

For formulations 1, 2, 5, 9, 10C, 12, and 12 C, the equations fit to the profiles had non-zero y-axis intercepts, i.e., at t=0, the % released was some positive number (the constant in the fitted polynomial). For simulation purposes, this was treated as an immediate release component, and that fraction was assumed to be released uniformly over the first 10 minutes after the lag time. Therefore, the release rate profiles show a "spike" in release over that 10 minutes, while the "% released" profile shows a sharp difference in slope between the first 10 minutes and the remainder of the 8 hours of release.

Enteric Coated Capsule Formulations

In some embodiments, the pharmaceutical composition can be formulated as an enteric coated capsule. Tables 8 and 9 provide a formulation for enteric coated capsule formulations.

TABLE 8

Capsule Contents

| Component | Amount (mg/capsule) |
|---|---|
| Capsule Contents | |
| Sodium nitrite, USP | 80 |
| Microcrystalline Cellulose, NF (Avicel ® PH 105) | 106.5 |
| Blue Food Coloring | 0.5 |
| Size #1 Capsule (Capsugel) | N/A |

TABLE 13

Coating Solution

| Component | Amount |
|---|---|
| Cellacefate, NF (Cellulose Acetate Phthalate) | 10 g |
| Triacetin, USP | 2.2 mL |
| 95% Ethanol/Acetone (1:1 Volume ratio) | 87.8 mL |

In this procedure, capsules were prepared by blending sodium nitrite, microcrystalline cellulose, and blue food coloring using standard blending methods for powders. The blended components were manually filled into size #1 capsule shells using small-scale capsule filling equipment. The finished capsules were tested for weight variation and content uniformity to meet compendia requirements for capsules.

The filled capsules were placed in a Procoater holder so that the cap side of each capsule was up. The coating tray was filled with coating solution to within one mm of the top. More coating solution was added to the tray, as needed, after each dip coating step.

The cap side of capsules was dipped into, and slowly removed from, coating solution. Excess coating solution was carefully wiped from the bottom of the capsules so that dried coating was symmetrical on the coating cap. Capsules were placed in a holder on a drying tray for 1 hour. The coating steps were repeated four more times for a total of five coatings.

After the coating was dried, the holder with the capsules was placed on a reversing stand with the cap side down (body side up) and the capsules were pushed into the lowest position with a coating tray cover. The body side of the capsules was dipped into a coating solution and slowly removed from the coating solution. The excess coating solution was carefully wiped from the bottom of the capsules so that the dried coating was symmetrical on the coating body. The capsules and holder was then placed on the drying tray for one hour. The coating steps were repeated four more times for a total of five coatings.

The enteric coated capsules were tested for sodium nitrate release. Uncoated capsules dissolved more than 75% in 0.1 N HCl (1 L) in 60 minutes at 37° C. using the USP paddle method at 50 rpm. In 750 mL 0.1 N HCl, enteric coated capsules released less than 1% sodium nitrite in 120 minutes at 37° C. using the USP paddle method at 50 rpm. After the pH of the solution was raised to 6.8 with the addition of 250 mL of 0.2 M tribasic sodium phosphate to the 750 mL 0.1 N HCl solution, the enteric coated capsules released more than 75% sodium nitrite in 60 minutes with 15-16 pancreatin added at 37° C. using the USP paddle method at 50 rpm.

Rabbit Pharmacokinetic Study

New Zealand rabbits with a weight of 3.0-3.2 kg were used for pharmacokinetic analysis of sustained release sodium nitrite formulations. One milliliter of blood was taken at 14 time points over a six hour period.

Initially, each rabbit was given 31 mg/kg of ketamine with 2 mg/kg of xylazine diluted in sterile normal saline i.m. A second i.m. injection of 0.5 mg/kg of acepromazine was also given at this time. As the rabbits lose consciousness, one ear was shaved with clippers. The area to insert the catheter was cleaned with an alcohol wipe and a 22 gauge iv catheter was inserted into the middle ear artery. A straight injection port was added to seal the end of the catheter. Blood was drawn with a 22 gauge needle and 500 µL of a 1 unit/mL heparin solution was immediately flushed through the catheter. This heparin flush was used after every blood draw.

Following the first blood draw, an 18 Pr gavage tube (36 cm long) was inserted down the esophagus of the rabbit. At the end of the gavage tube, the nitrite capsule is inserted and quickly pushed into the stomach with 15 mL of air. Three formulations were tested: formulations 100A, 200A, and 300A. The gavage tube was then removed and the remaining blood was taken over the next six hours.

The blood draw was equally divided into two 1.5 mL micro centrifuge tubes. 100 µL of plasma nitrite preservation solution was immediately added to one aliquot, while the other aliquot was spun at 5,000 rpm for 2 minutes to separate out plasma that was then combined with 200 µl of plasma nitrite preservation solution. All samples were stored in liquid nitrogen until processing.

Figure 11:
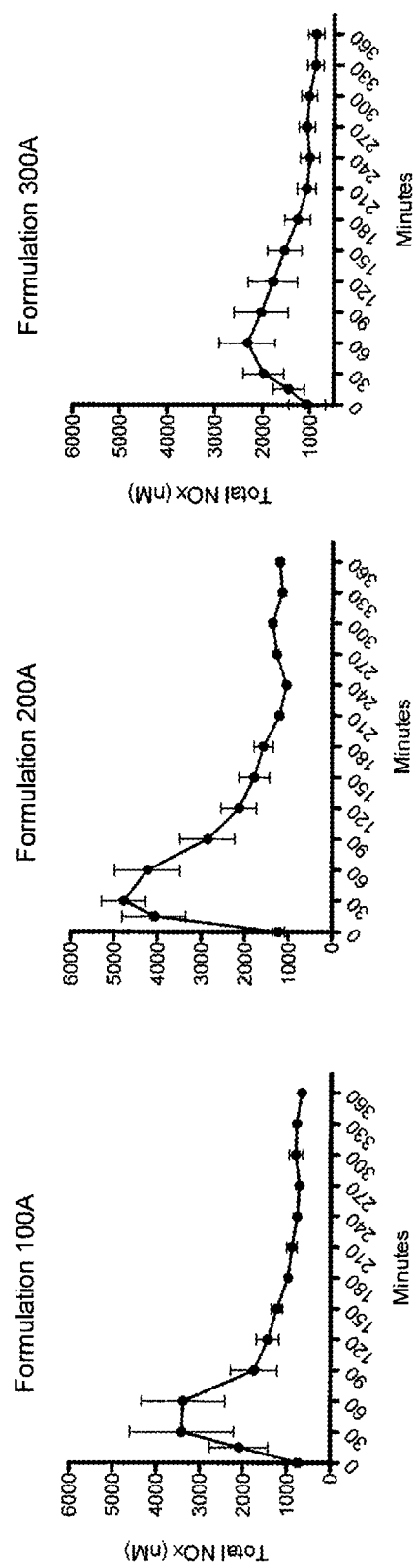
FIG. 11 shows the release profile of total NOx for formulations 100A, 200A, and 300A in rabbits.
Figure 12:
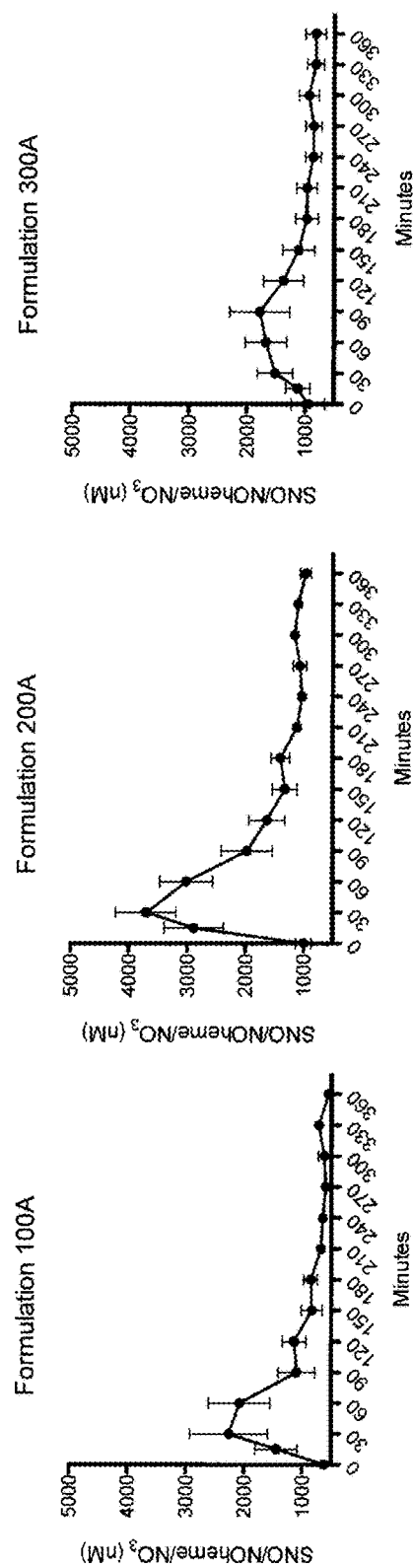
FIG. 12 shows the release profile of nitrate, nitrosothiols, nitrosoheme, and nitrosamines for formulations 100A, 200A, and 300A in rabbits.
Figure 13:
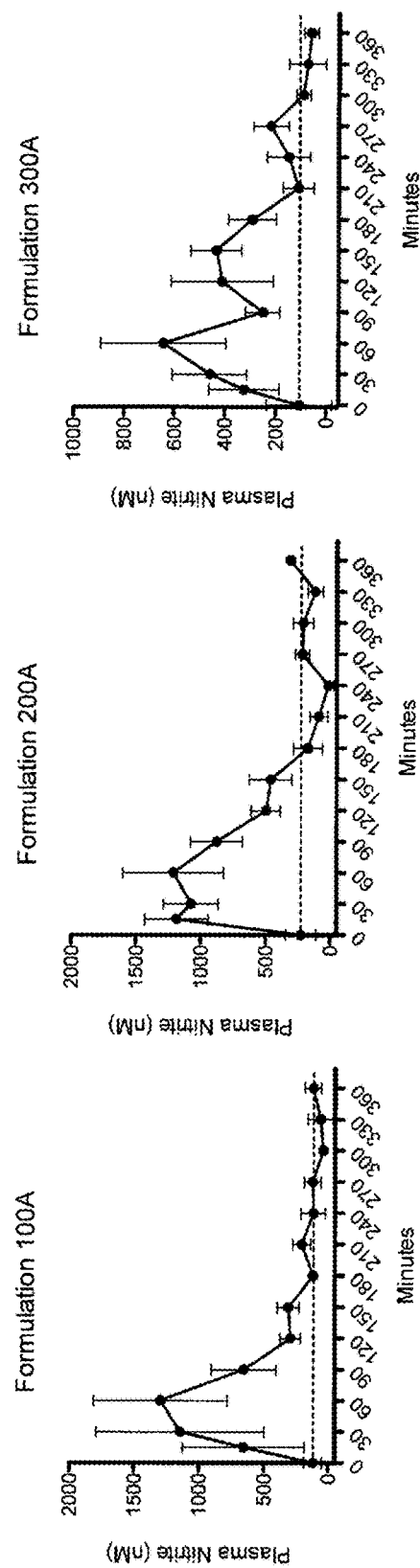
FIG. 13 shows the release profile of free nitrite for formulations 100A, 200A, and 300A in rabbits.

The plasma nitrite preservation solution included:
7.85 grams KFeCN+25 mL of PBS=1
66 mg NEM+3 mL of PBS=2
1.5 mL of nonidet P40=3
1 (21 mL)+2 (2.5 mL)+3=nitrite preservation solution Total NOx in the plasma was calculated as described below. The time courses for each of the three tested formulations are shown in FIG. 11. Additionally, the amount of free nitrite was calculated by treating the samples with 580 mM sulfanilamide in 1N HCl for 15 minutes. This treatment scavenges the free nitrite, leaving behind nitrate, nitrosothiols, nitrosoheme, and nitrosamines. The amount of these remaining components, determined using the method described below, is shown in FIG. 12. When this amount is subtracted from the amount of total NOx, the resulting number reflects the amount of free nitrite (FIG. 13). The data for formulations 200A and 300A represent the mean of five rabbits, while the data for formulation 100A represent the mean of four rabbits, as one rabbit administered the latter formulation experienced a clogging of its arterial catheter during the study.

Nitric Oxide Chemiluminescence Detection

A Sievers 280i Nitric oxide analyzer (NOA) was used to construct a standard curve of nitrite/NO concentrations and to measure specimen total NOx, nitrosothiols (SNO)+nitrosoheme+nitrate, and free nitrite. To measure nitrite, the purge vessel contained a reducing agent (2 mL sodium iodide in 7 mL glacial acetic acid) to reduce nitrite, nitrate, and nitroso compounds to free nitric oxide. NO gas is then detected in the NOA through a reaction with ozone emitting a photon of light which is detected by the chemiluminescence detector. The amount of NO present was determined by integrating the emission signal over time and calibrated against known amounts of sodium nitrite (0, 0.1, 0.5, 1, 10 and 100 µM) as a source standard for NO. Plasma nitrite was determined by reacting an aliquot of plasma with 580 nM sulfanilamide in 1N HCl for 15 min to scavenge free nitrite. The total amount of free nitrite was determined by subtracting the sulfanilamide value from the total NOx value.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A method for treating peripheral neuropathy in a human, the method comprising orally administering two times per day for at least three days a solid, sustained release pharmaceutical composition comprising about 40 mg of sodium nitrite, or a pharmaceutically acceptable salt thereof, and a binding agent, wherein the pharmaceutical composition is coated with an enteric coating.

2. The method of claim 1, wherein the sodium nitrite is not substantially released in the stomach of the human.

3. The method of claim 1, wherein the sustained release pharmaceutical composition is administered for at least seven days.

4. The method of claim 1, wherein the sustained release pharmaceutical composition is administered for at least ten days.

5. The method of claim 1, wherein the binding agent is sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethlene glycol.

6. The method of claim 5, wherein the binding agent is hydroxypropyl methylcellulose, microcrystalline cellulose, or polyvinyl pyrrolidone.

7. The method of claim 1, wherein the enteric coating comprises a polymer selected from cellulose acetate phthalate, hydroxypropylmethylcellulose acetate succinate, methacrylate acid copolymers, cellulose acetate trimellitate, polyvinyl acetate phthalate, hydroxyethylcellulose phthalate, and hydroxypropyl methylcellulose phthalate.

* * * * *